United States Patent [19]
Bunnelle et al.

[11] Patent Number: 5,627,229
[45] Date of Patent: *May 6, 1997

[54] HOT MELT ADHESIVE HAVING CONTROLLED PROPERTY CHANGE

[75] Inventors: William L. Bunnelle, Hugo Township; Christopher M. Ryan, Chisago City, both of Minn.

[73] Assignee: H.B. Fuller Licensing & Financing, Inc., St. Paul, Minn.

[*] Notice: The portion of the term of this patent subsequent to Mar. 1, 2015, has been disclaimed.

[21] Appl. No.: 397,377

[22] Filed: Mar. 2, 1995

Related U.S. Application Data

[62] Division of Ser. No. 919,999, Jul. 27, 1992, abandoned, which is a continuation of Ser. No. 385,315, Jul. 25, 1992, abandoned.

[51] Int. Cl.$^6$ .............................. C09J 9/00; A61C 19/02; B65D 77/02; B65D 21/00
[52] U.S. Cl. .......................... 524/270; 206/438; 206/449; 206/813; 229/100; 229/120.01; 156/327
[58] Field of Search .......................... 524/270–72, 274, 524/292–94, 518, 524–25; 206/438, 449, 813; 229/100; 156/327

[56] References Cited

U.S. PATENT DOCUMENTS

| | | | |
|---|---|---|---|
| 3,318,977 | 5/1967 | Battersby et al. | 260/889 |
| 3,615,106 | 10/1971 | Flanagan et al. | 281/21 |
| 3,932,326 | 1/1976 | Hoh et al. | 260/26 |
| 3,971,883 | 7/1976 | Meeks et al. | 174/120 |
| 3,982,051 | 9/1976 | Taft et al. | 427/207 |
| 4,028,292 | 6/1977 | Korpman | 260/27 |
| 4,035,218 | 7/1977 | Yount | 156/289 |
| 4,080,347 | 3/1978 | Hefele | 250/18 |
| 4,195,556 | 4/1980 | Gallagher et al. | 93/58 |
| 4,284,542 | 8/1981 | Boyce et al. | 260/27 R |
| 4,293,473 | 10/1981 | Eastman | 260/27 |
| 4,299,930 | 11/1981 | Boggs | 525/74 |
| 4,359,540 | 11/1982 | McEntire et al. | 521/129 |
| 4,497,936 | 2/1985 | Tancrede et al. | 525/222 |
| 4,622,357 | 11/1986 | Tsuchida et al. | 524/270 |
| 4,627,847 | 12/1986 | Puletti et al. | 604/366 |
| 4,717,749 | 1/1988 | Tang et al. | 524/271 |
| 4,734,447 | 3/1988 | Hattori et al. | 524/271 |
| 4,745,026 | 5/1988 | Tsukahara et al. | 428/323 |
| 4,767,813 | 8/1988 | Evitt | 524/271 |
| 4,895,567 | 1/1990 | Colon et al. | 604/361 |
| 5,026,756 | 1/1991 | Arendt | 524/293 |

*Primary Examiner*—Edward J. Webman
*Attorney, Agent, or Firm*—Carolyn A. Fischer

[57] ABSTRACT

The novel adhesives of this invention contain a blend of components that result in the adhesive having a physical property that changes at a controlled rate as a function of time after application until it reaches a final equilibrium value.

The adhesives can contain a thermoplastic polymer base, a tackifying resin, and an aromatic plasticizer optionally in combination with other ingredients. The plasticizer tackifier combination is chosen such that the tackifier/plasticizer interaction causes the initial value of the physical property after application to change, at a controlled rate, to a final equilibrium level.

5 Claims, 20 Drawing Sheets

HOT MELT ADHESIVE HAVING CONTROLLED PROPERTY CHANGE

This is a division of application Ser. No. 07/919,999, filed Jul. 27, 1992, now abandoned, which is a continuation of application Ser. No. 07/385,315, filed Jul. 25, 1992 now abandoned which applications are incorporated herein by reference.

FIELD OF THE INVENTION

The invention relates to a novel class of hot melt adhesives that can exhibit a controlled property change when cooled after application. The adhesives can be used to form high quality permanent bonds or can be used to form "fugitive bonds." Permanent bonds can exhibit highly cohesive, tensile, peel and shear strength sufficient to maintain the mechanical integrity of a structure manufactured with the adhesive. Such adhesives can be used in a variety of construction applications such as in composite articles or on hard to stick surfaces such as fluorocarbons or high clay filled surfaces. A fugitive bond is formed by an adhesive that is formulated to form an initially strong cohesive bond under peel and shear but, after time, changes to a brittle bond that has significant shear strength but has little peel strength. Such adhesives can be used in a variety of end uses including easily opened case and carton sealing adhesives, can and bottle labeling adhesives, pallitizing adhesives, etc.

BACKGROUND OF THE INVENTION

Thermoplastic hot melt adhesives of the prior art typically comprise a thermoplastic polymer, a tackifier, a wax or plasticizing oil, and other optional ingredients. In large part, hot melt adhesive development in recent years has focused on the thermoplastic polymer used as the adhesive base material. Many inventions are based on finding a new property in a new thermoplastic polymer/adhesive composition or finding a new use for a known adhesive. A large variety of literature is directed to various thermoplastic polymers such as ethylene/vinyl acetate, ethylene methacrylate, atactic polypropylene, A—B—A block copolymers, A(BA)$_n$B block copolymers, etc. A brief selection of such literature includes:

Skeist, *Handbook of Adhesives*, Van Nostrand Reinhold Co. Inc. (1977).

Battersby et al., U.S. Pat. No. 3,318,977, teaches thermoplastic adhesives containing polyethylene, isobutylene rubber, tackifier resins, and ethylene-vinyl acetate copolymers.

Meeks et al., U.S. Pat. No. 3,971,883, teaches crosslinkable ethylene vinyl acetate copolymer resins in adherent laminates.

Taft et al., U.S. Pat. No. 3,982,051, teaches hot melt adhesive compositions containing ethylene/vinyl acetate and/or alkyl acrylate copolymers in hot melt carpet backing adhesives.

Boggs, U.S. Pat. No. 4,299,930, teaches hot melt adhesives containing modified polyethylenes and ethylene vinyl acetate copolymer and other materials.

Eastman, U.S. Pat. No. 4,293,473, teaches polyvinyl alcohol or ethylene vinyl alcohol copolymers in crystalline solvent based systems for bonding cellulosics, spun bonded polyolefins, aluminum foil, and other substrates.

Flanagan et al., U.S. Pat. No. 4,345,349, teaches a combination of an A—B—A block copolymer and ethylene vinyl acetate polymer and other standard hot melt ingredients to form an adhesive for book binding.

Tancrede et al., U.S. Pat. No. 4,497,936, teaches ethylene-vinyl acetate copolymers in combination with olefin rubbers in hot melt adhesives.

The adhesives disclosed in the typical prior art publications are adhesives that are applied as a melt liquid, and when cooled to ambient temperature become a solid. Once cooled, the adhesive mass attains relatively stable properties such as peel strength, shear strength, cold flow, or storage modulus, also known as G'. In other words, upon cooling, the adhesive formulation rapidly reaches a near equilibrium condition with respect to its physical state. As a result, each physical property rapidly attains the vast majority of its values immediately when cooled. We will refer to this state immediately after a hot melt adhesive cools and attains near equilibrium properties as the "ambient state" of the hot melt adhesive.

In the conventional production of prior art work pieces or articles, conventional hot melt adhesives are typically extruded at elevated temperature directly onto a bond site. The second substrate must be combined with the adhesive relatively quickly while the adhesive is still molten or liquid, or the adhesive will cool, harden, and set, making it impossible for the melt to wet the second substrate to form a bond. When the molten adhesive is extruded in a form of hot molten bead onto a porous substrate, the adhesive can wet or soak into one or more porous substrate and adhere the substrate to another substrate by entrapping fibers in the cooled adhesive mass. In such hot melt technology, the molten adhesive retains sufficient heat such that the material can retain a low melt viscosity, low modulus, and can penetrate or wet components of a work piece to ensure secure bonding before cooling. As such adhesives cool, the properties rapidly reach a final ambient state and, once the final values are reached, have, for the most part, stable values for that adhesive blend at ambient temperatures. However, such adhesives have the drawback that bonds must be made while the adhesive is at an elevated temperature to insure proper bonding, which prevents their use on heat sensitive substrates.

Pressure sensitive adhesives have been developed based on thermoplastic elastomers and a large variety of patents are directed to elastomeric based adhesives. A brief selection of such patents include:

Collins et al, U.S. Pat. No. 4,136,699, teaches a disposable article using a hot melt pressure-sensitive adhesive as a positioning or a construction material. Such adhesive is typically extruded to high temperature onto materials of construction during manufacture.

Chen et al, U.S. Pat. No. 4,460,364, teaches hot melt pressure-sensitive adhesives used in the manufacture of sanitary products.

Schmidt Jr., et al, U.S. Pat. No. 4,526,577, teaches the use of styrene-butadiene-styrene block copolymers in the manufacture of disposable laminates using multi-line extrusion adhesive technology.

Puletti et al, U.S. Pat. No. 4,627,847, also teaches the use of hot melt adhesives and disposable article construction.

Elastomeric based products have been developed which exhibit the property of pressure sensitivity. These types of products can form a bond after cooling, but generally do not cold flow after the adhesive reaches the ambient state. These elastomeric based pressure sensitive products are unable to form mechanical bonds or physically entrap fibers of a porous substrate after they are cooled and reach their ambient state. They tend to form surface bonds from the pressure sensitive nature of the adhesive.

Adhesives having properties that vary after application and cooling would offer significant advantages. In certain applications, initial bond strength is important, while after a time, the bond strength is preferably reduced. In other applications, fluidity is important while, after a time, the compositions are preferably in solid form. In still other applications, initial bond strength is not critical, while a high final bond strength is critical.

Accordingly, a substantial need exists in the industry for an adhesive that can have a controlled change in important properties after application. In other words, a need exists for an adhesive that does not reach a final equilibrium value for one or more physical properties until well after application and cooling.

In one aspect, a controlled change in modulus can provide important advantages. After application and cooling, the modulus of the adhesive is at an intermediate state between the modulus of the molten mass and the final modulus and is significantly below the modulus of typical comparable prior art hot melt adhesives. Such an adhesive with a controlled change or increase in modulus (G') can initially obtain significant cold flow after application that aids in construction of a variety of work pieces. Such cold flow can cause the adhesive to flow into a fabric to cause the physical entrapment of the materials of construction in the adhesive mass resulting in the formation of a bond of high integrity when the adhesive reaches its modulus potential. Such cold flow can also cause rapid and enhanced surface wetting of a nonporous surface producing enhanced bonding when fiber entrapment is not involved. Further, the bond can significantly resist the effects of a number of debonding mechanisms, including the presence of moisture or other compositions that can reduce or eliminate bond strength. After a time, the modulus increases to a final high equilibrium value forming strong cohesive bonds.

In recent years, increasing attention has been directed to the development of hot melt adhesives that can be sprayed onto the work piece or substrate during a manufacturing regimen. The use of spray-on adhesives has been found to increase productivity. Conventional spray-on adhesives are sprayed from a plurality of narrow orifices in a form of a fiber, a thread, a filament, or a plurality thereof, having a substantially circular cross-section with a diameter of 0.01" to 0.04". The spray-on adhesive fiber has substantial surface area in comparison to the mass or volume of the fiber. As a result, the sprayed adhesive fiber cools very rapidly upon contact with the ambient atmosphere. However, the spray-on adhesive, even if it retains some residual heat, attains the ambient temperature very quickly upon contact with the work piece. By ambient temperature, we mean the temperature of the surrounding atmosphere and the temperature of the work piece in the construction locale. This is in sharp contrast to extruded hot melt adhesives that retain significant amounts of heat for a period after application. Most conventional spray-on adhesives require a heated air flow at a temperature exceeding 250° F., which is above the $T_g$ of styrene in the block copolymers used in the adhesive. Such a temperature is required to keep the adhesive molten until applied. In these spray-on adhesive applications, the temperature of the work piece and the manufacturing locus (not including the application equipment) are typically not substantially different. Conventional spray-on adhesives, after their application of work pieces, typically form a solid mesh or a web which is the result of the pattern in which the spray-on adhesive is applied to the substrate. An overlapping application pattern, as it is directed onto a moving web, typically takes the form of overlapping circles or ovals of adhesives that form a continuous adhesive strip or layer.

In another aspect, an adhesive with controlled bond strength can be important in a pallitizing adhesive and a carton-sealing adhesive which can have easily opened bonding. In such applications, initial peel and shear strength are important to secure the components in place. After assembly, the adhesive bond needs only sufficient shear strength to maintain the integrity of the assembly. At a use locus, the carton adhesive and the palletizing adhesive preferably have low peel strength permitting easy opening of the carton or easy disassembly of the pallet.

BRIEF DISCUSSION OF THE INVENTION

Figure 1:
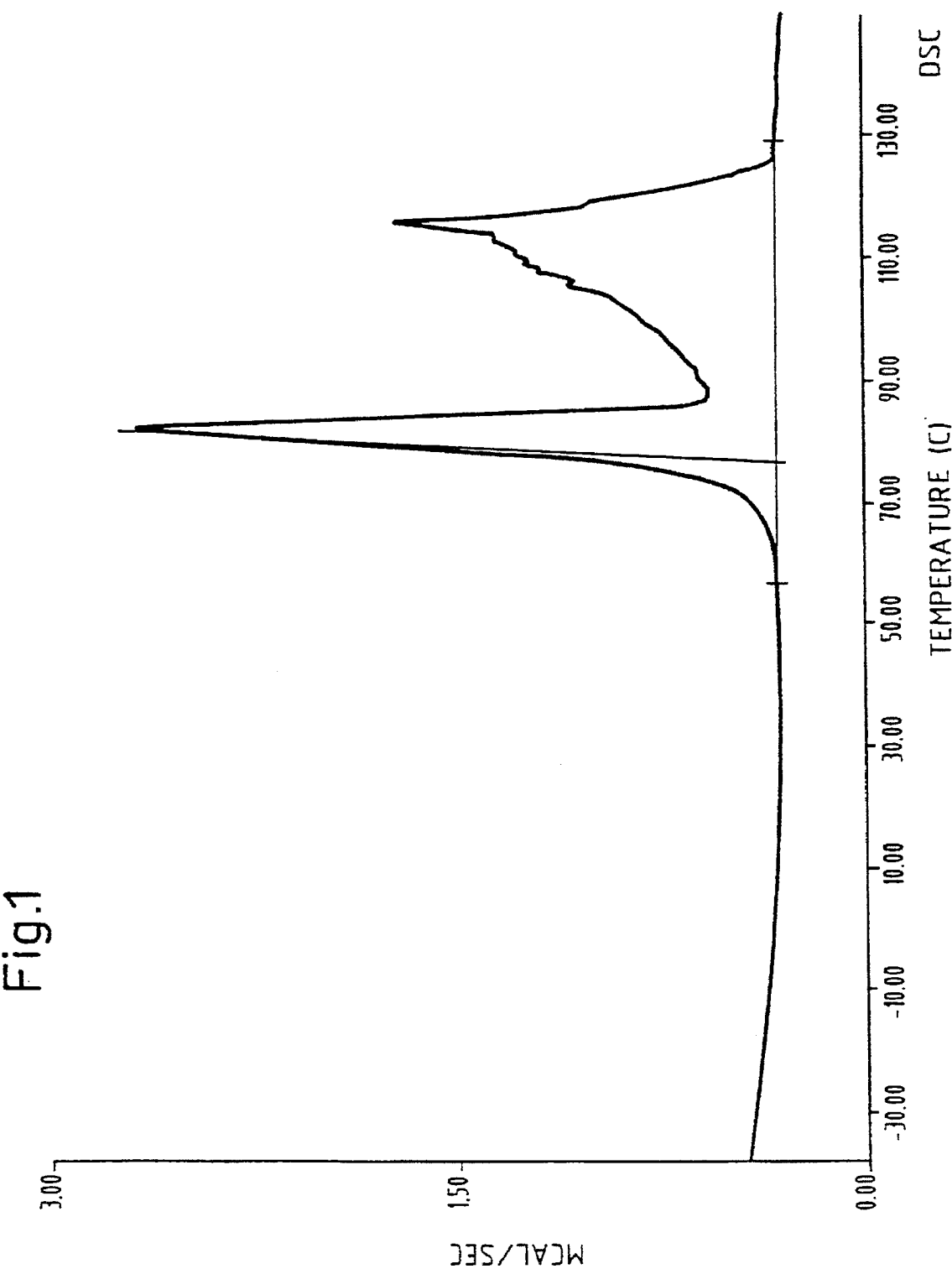
FIG. 1–4 and 5–20 are respectively melt profiles of BENZOFLEX-252 and the invention obtained by differential scanning calorimetry.
Figure 2:
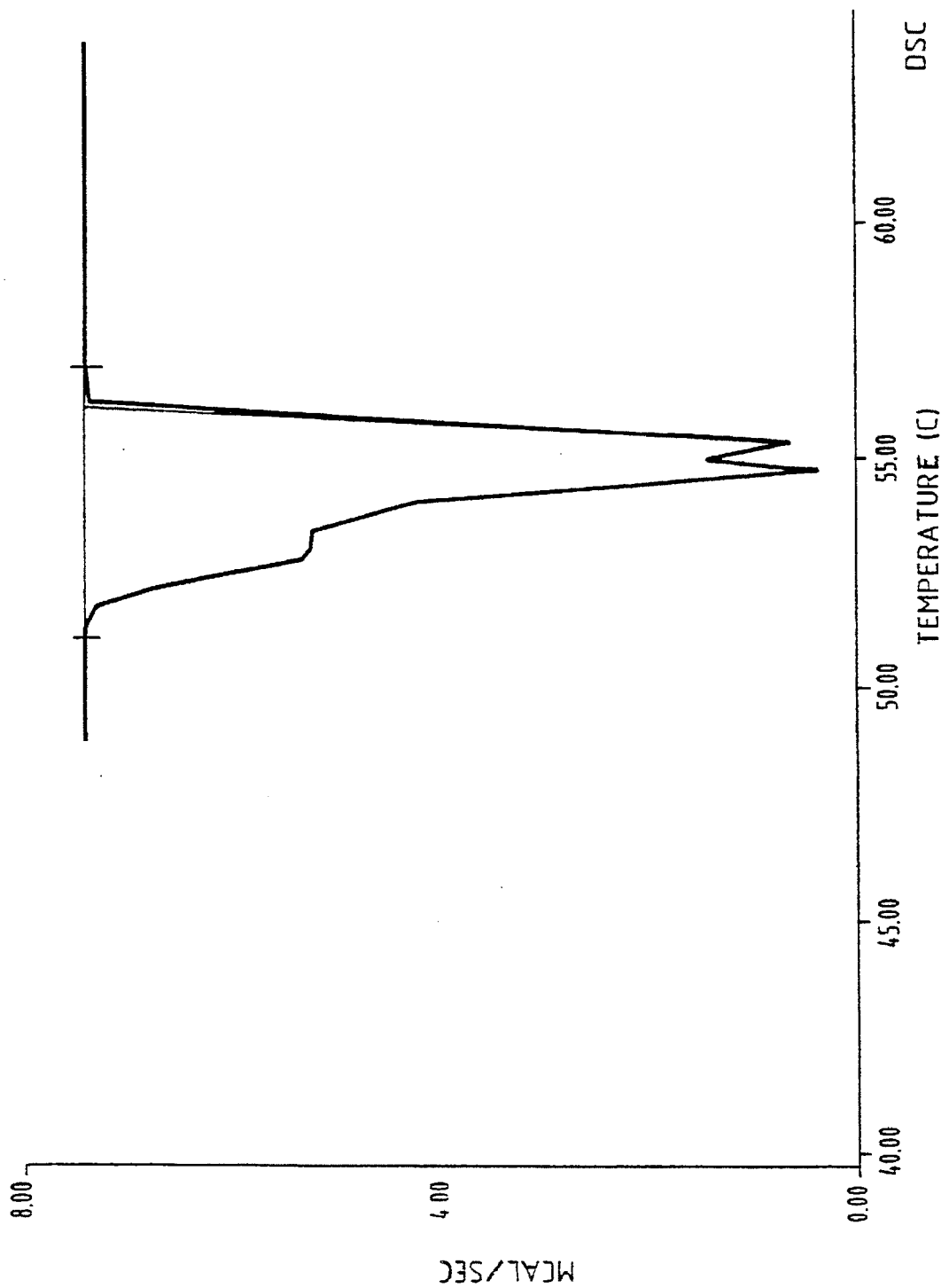
Figure 3:
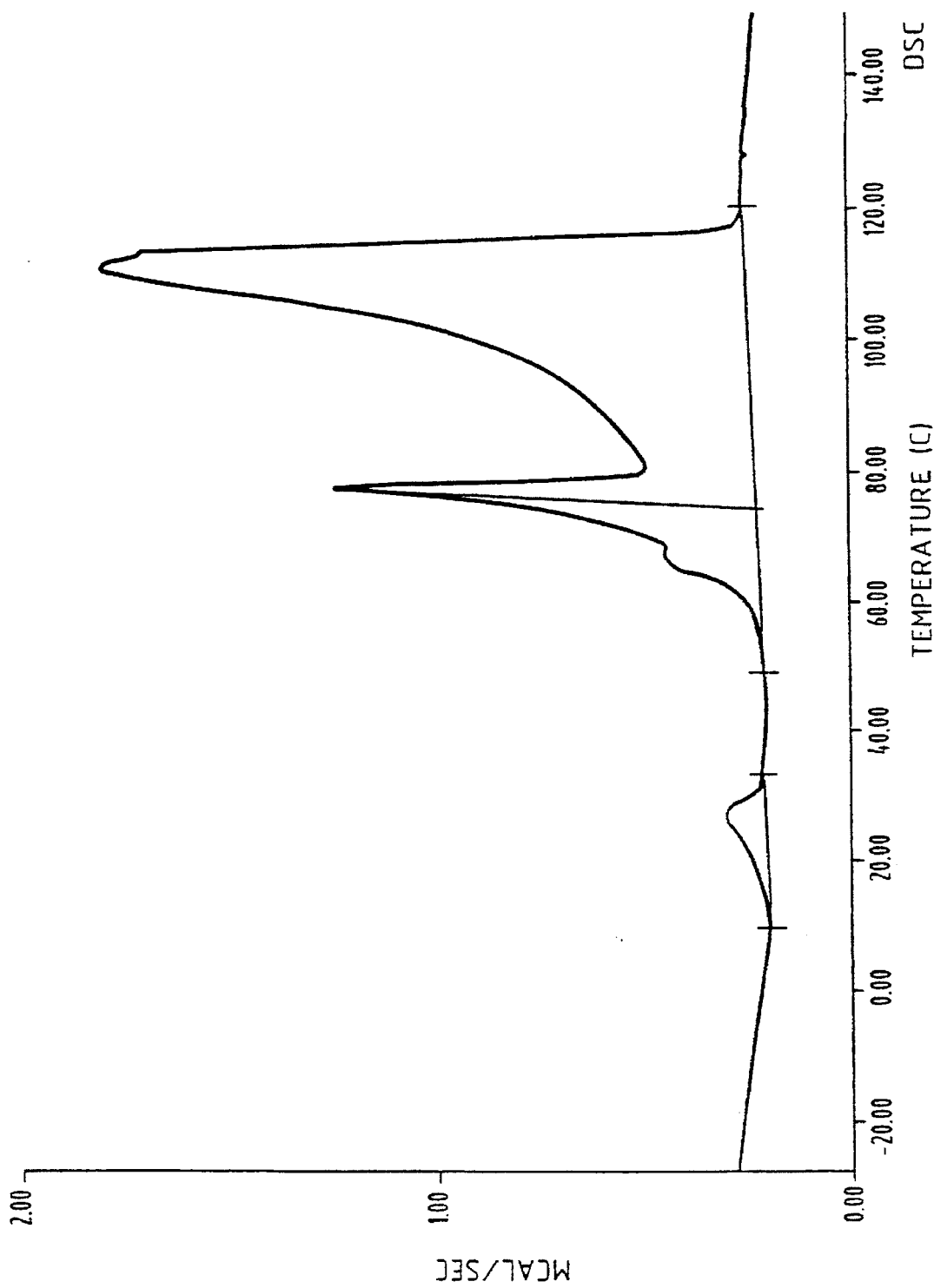
Figure 4:
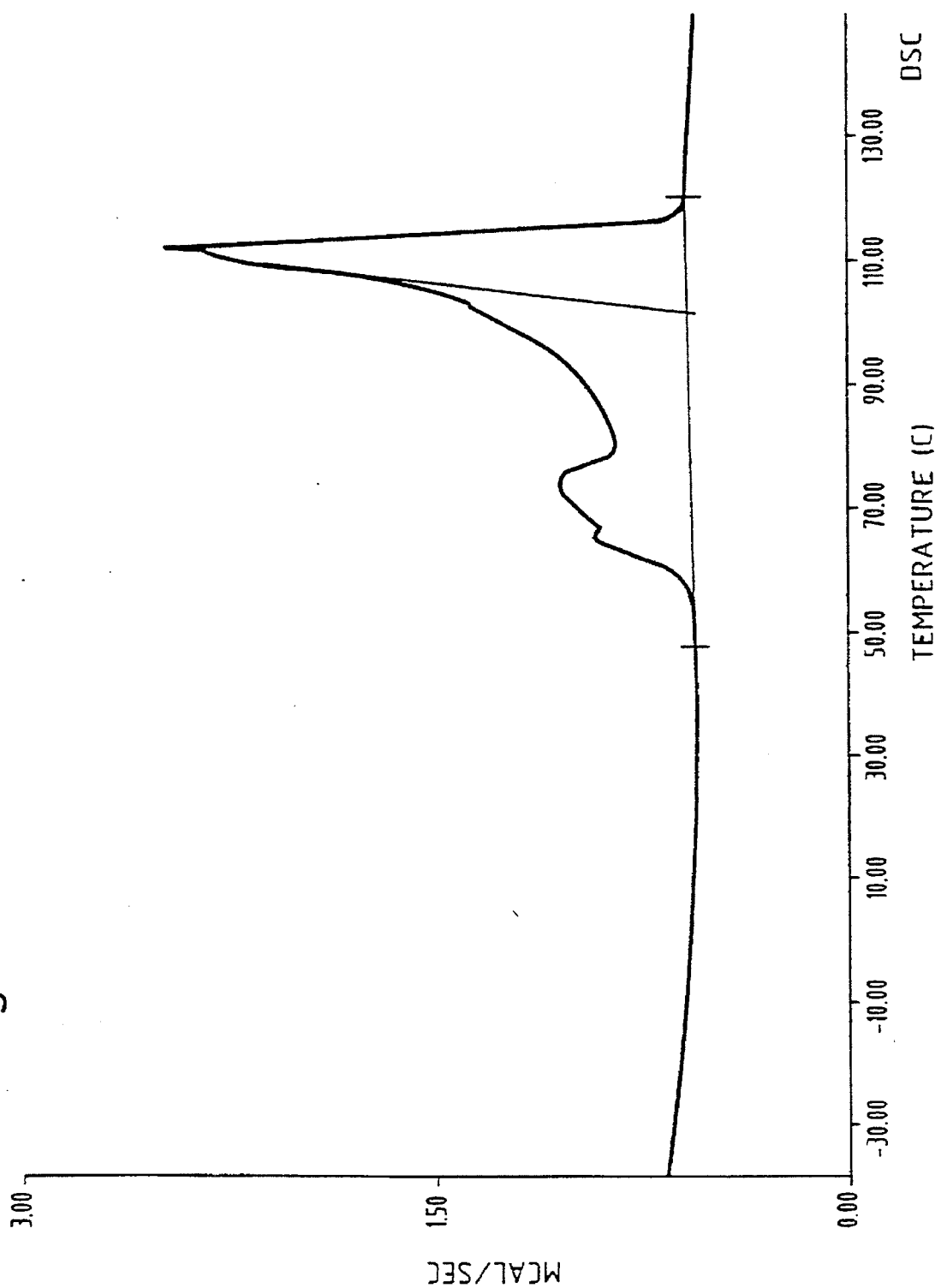
Figure 5:
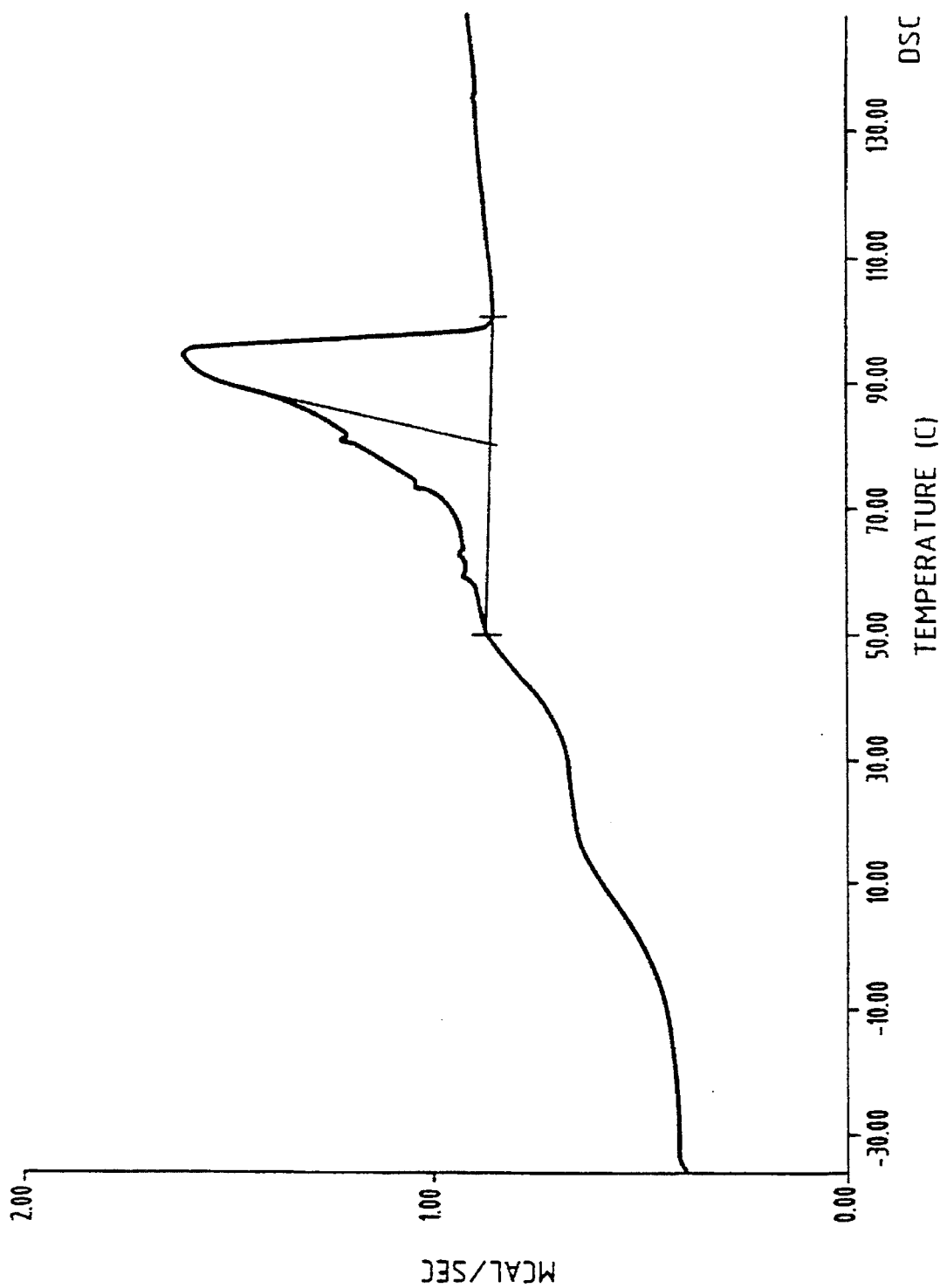
Figure 6:
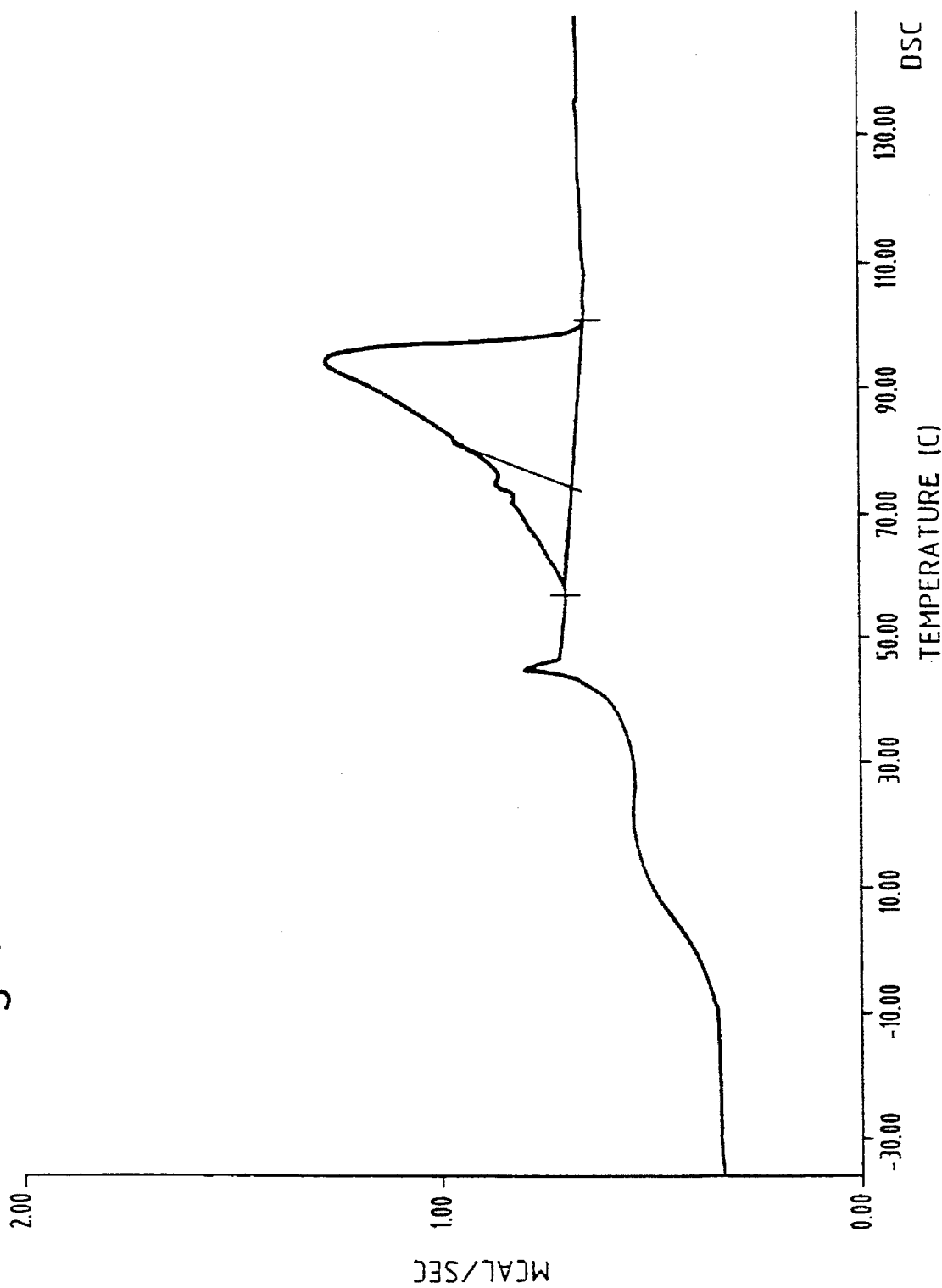
Figure 7:
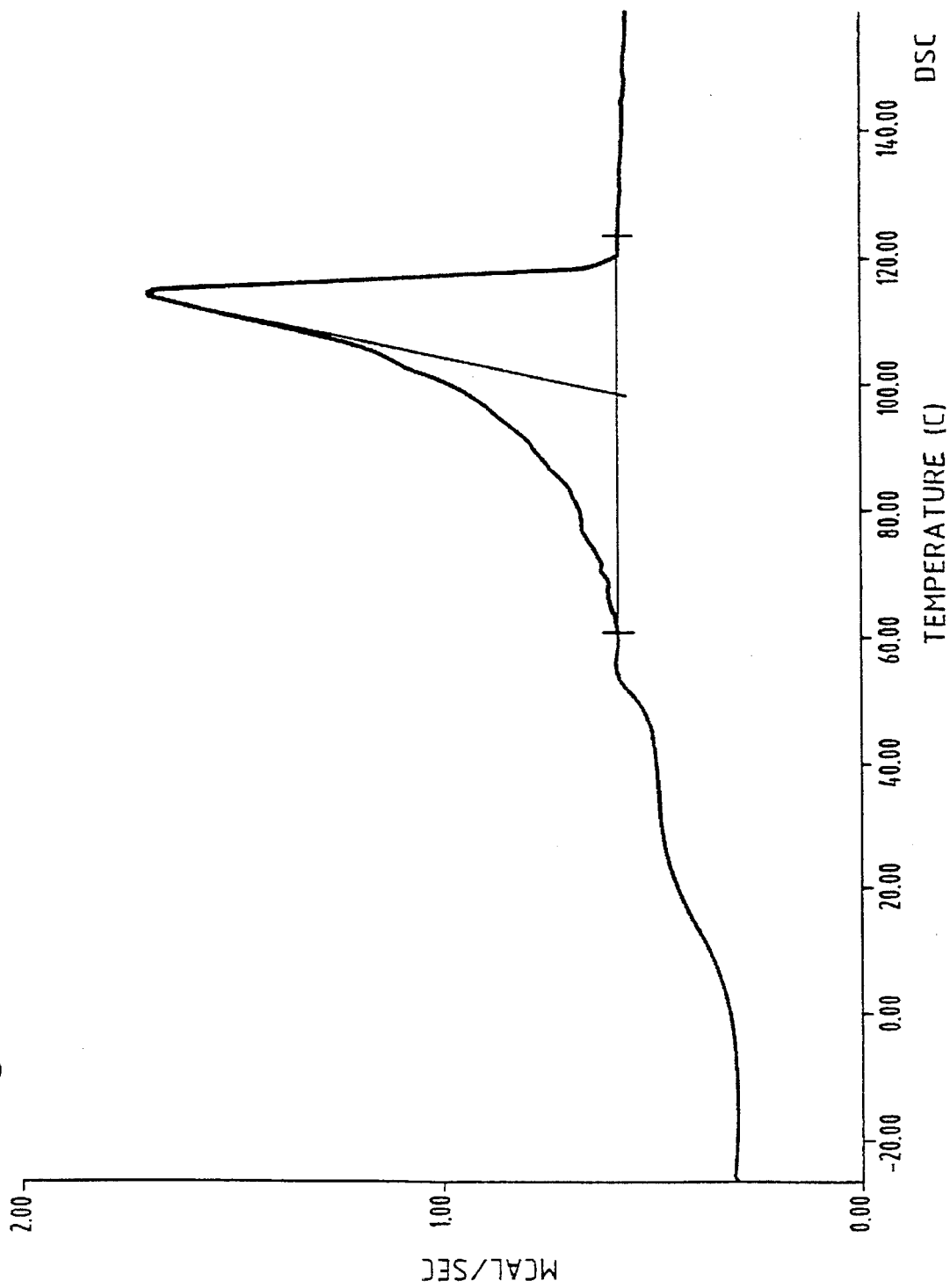
Figure 8:
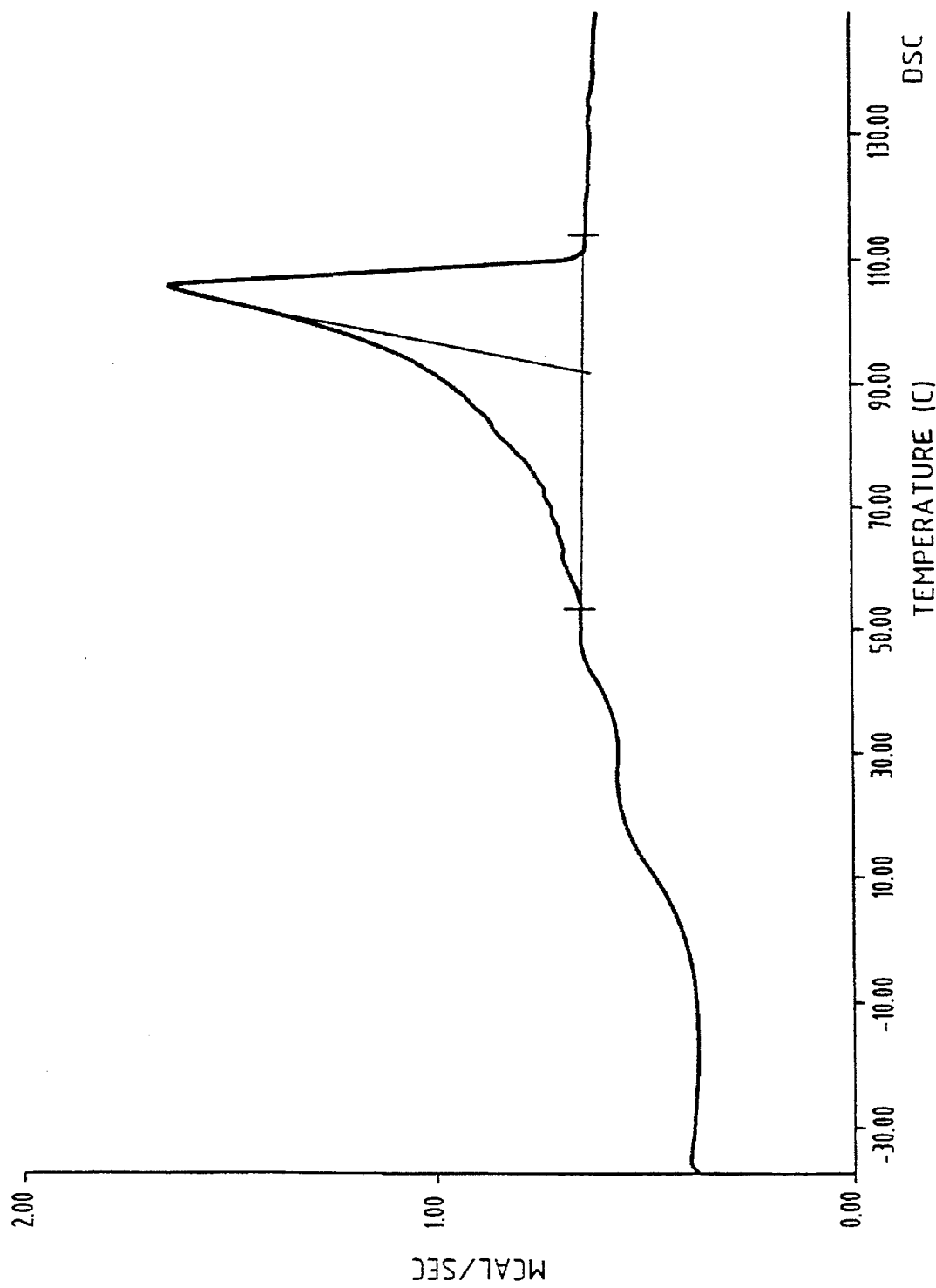
Figure 9:
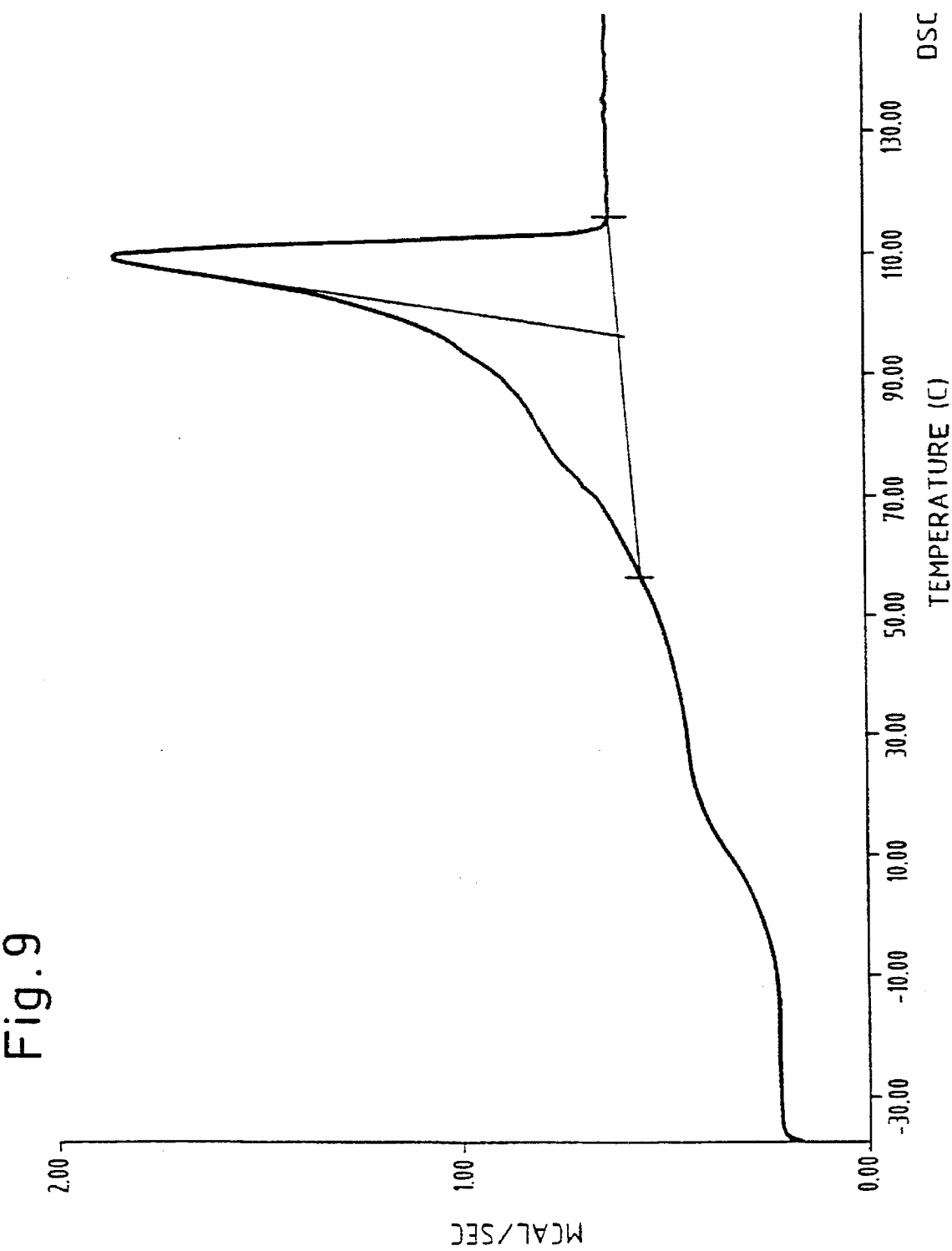
Figure 10:
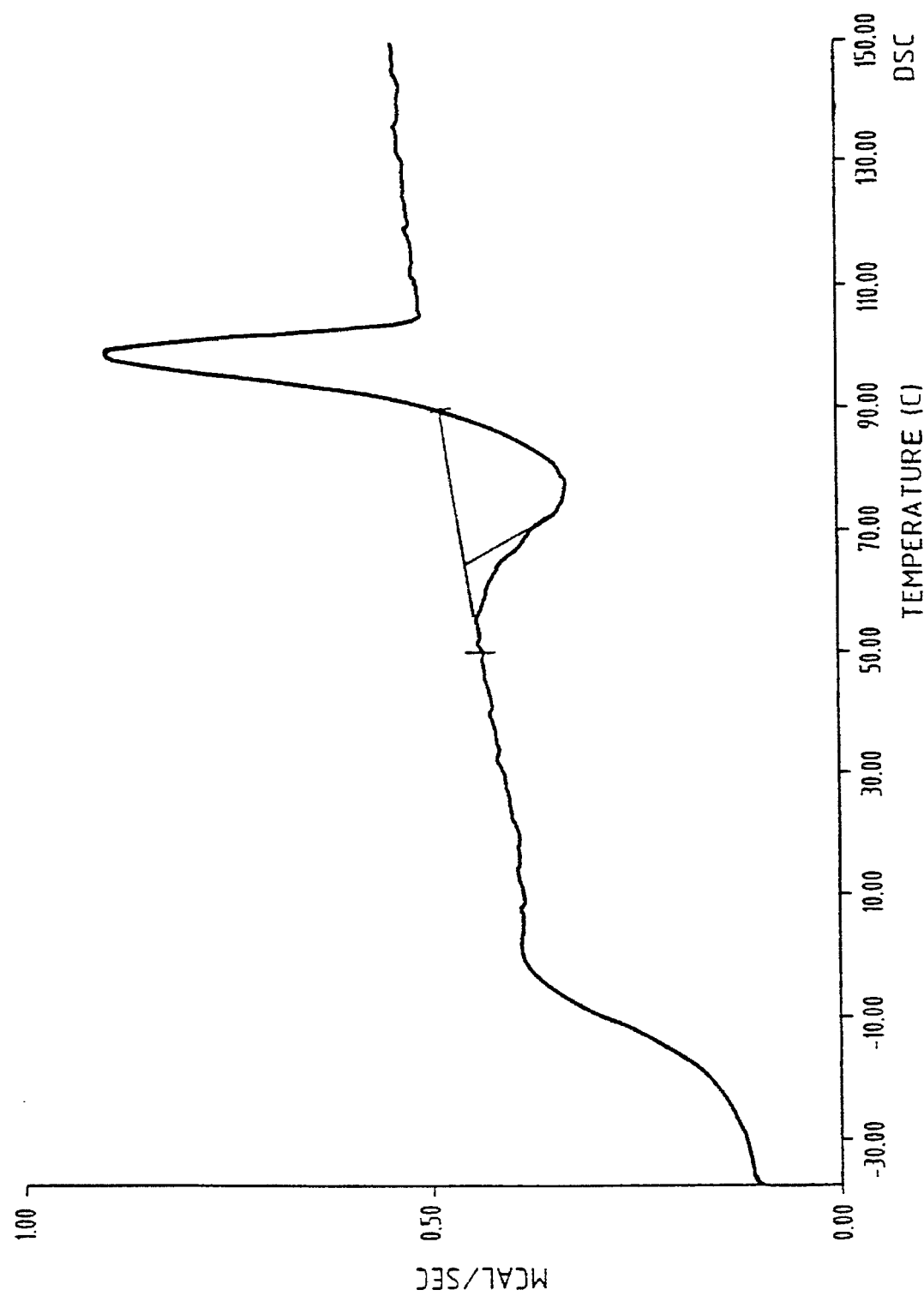
Figure 11:
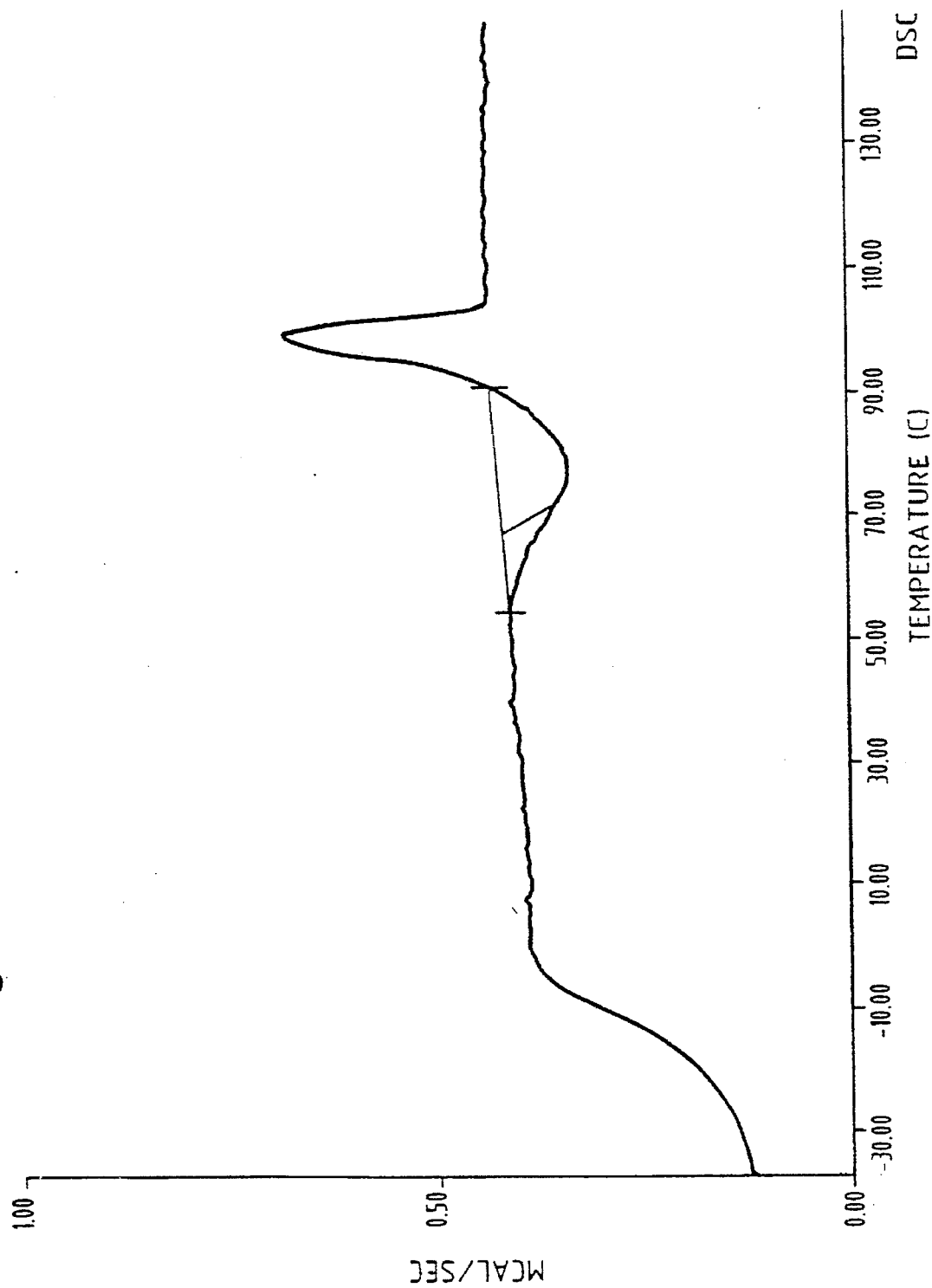
Figure 12:
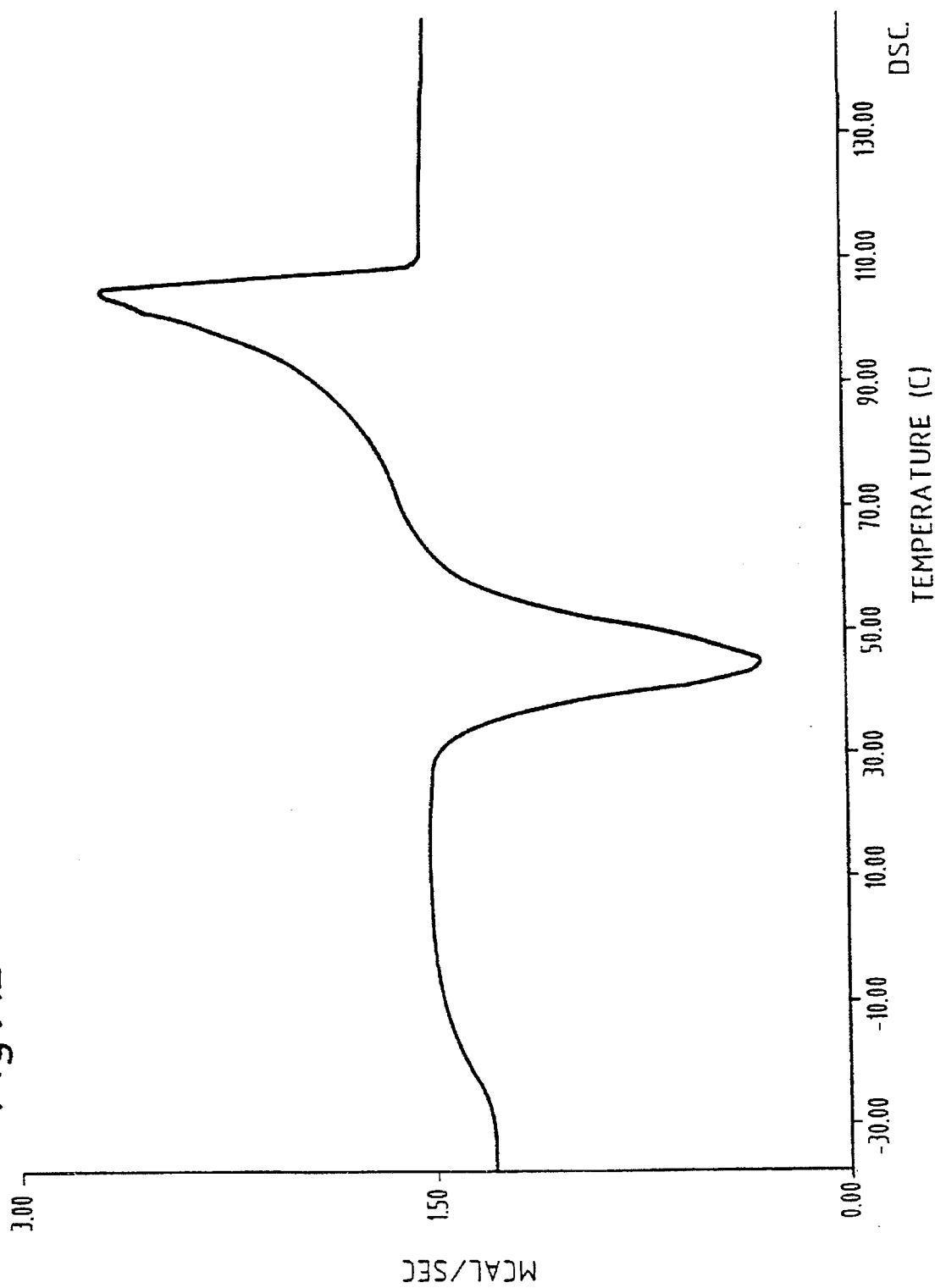
Figure 13:
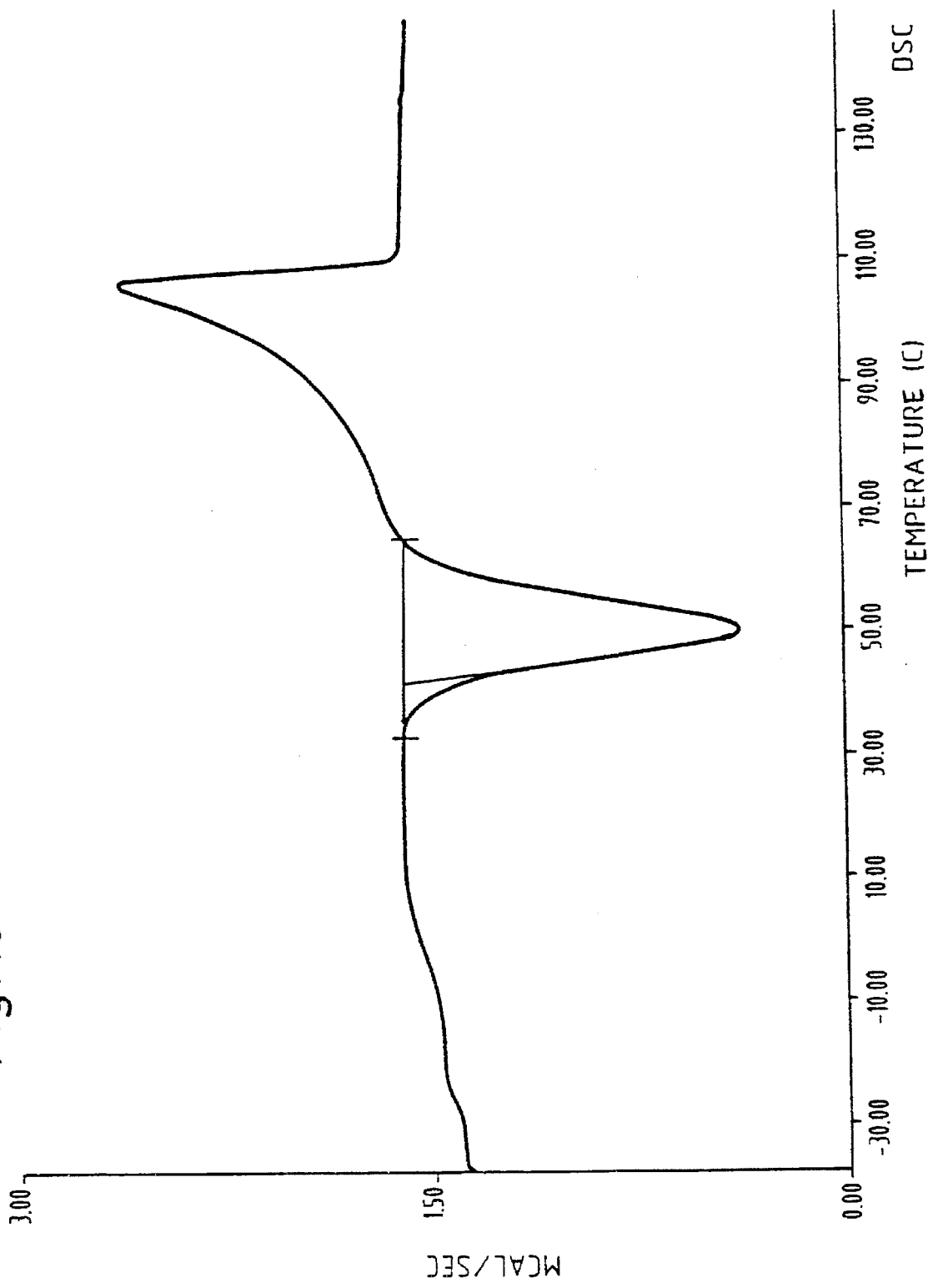
Figure 14:
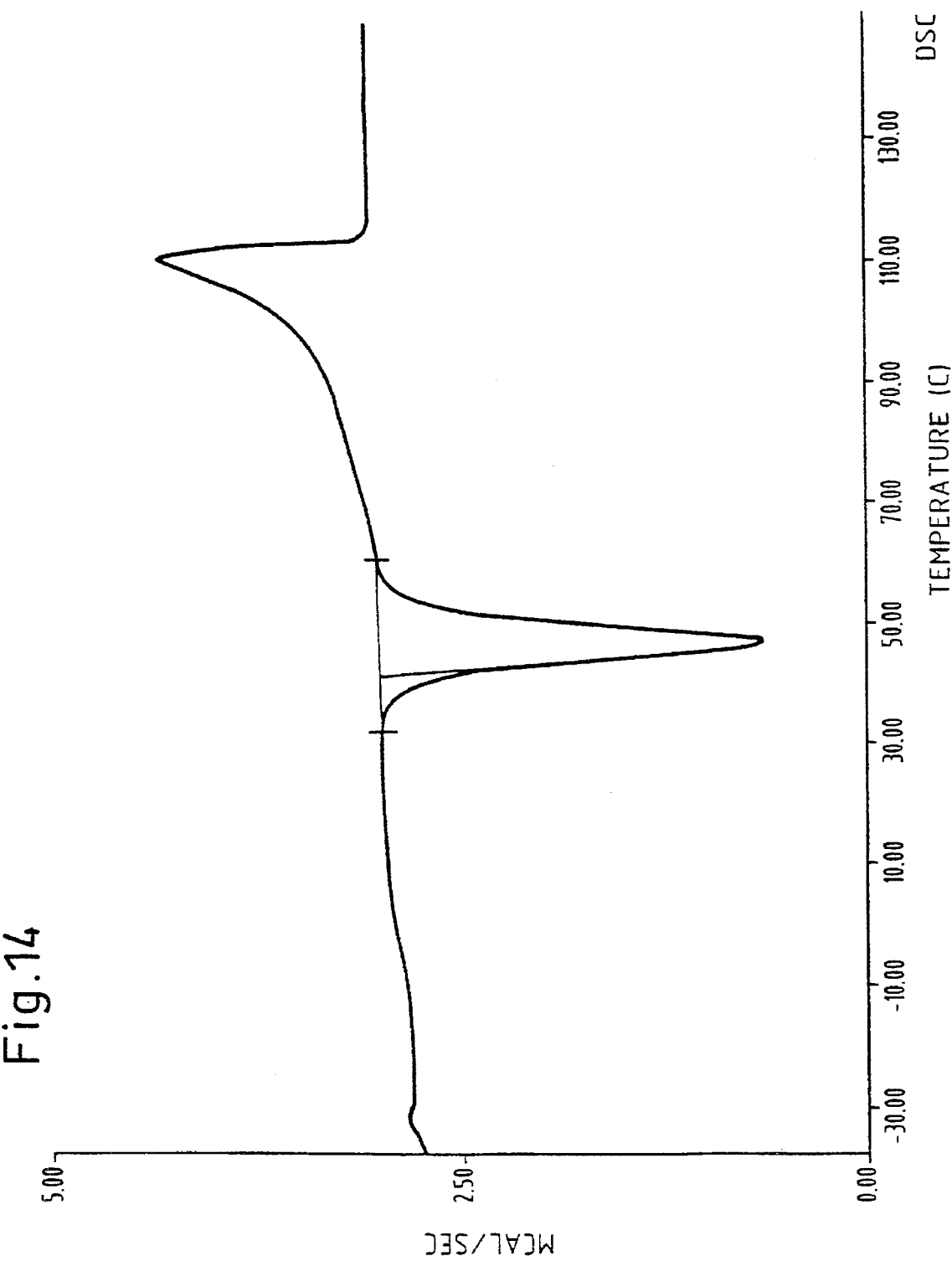

We have found a novel class of adhesive compositions containing proportions of a tackifier and an aromatic plasticizer that are selected by using selective compatibility to produce, in the adhesive, properties that vary after application. The adhesive, when applied and cooled, exhibits one or more physical properties that do not attain a final or equilibrium value (ambient state) until at least 5 minutes after application and cooling. By final or equilibrium value, we mean the value of a physical property after the vast majority of changes in the property and the vast majority of changes in the adhesive mass have occurred.

The adhesives of the invention can have any arbitrary amount of thermoplastic polymer. At a typical polymer content, the adhesive, when first applied, has low modulus, while the final bonds obtain significantly high equilibrium modulus, peel and shear strength. At no polymer to low relative polymer concentration, the initial bonds have sufficient tack, peel strength and shear strength to hold the substrates together and act as case or carton sealing adhesives, but at equilibrium tend to have poor peel strength but have sufficient modulus for many label pickup or case and carton adhesive application. The low peel strength and brittle nature of these low polymer adhesives result in a palletizing adhesive of easy release from the pallet and easy opening case or carton adhesive, otherwise known as a fugitive bond.

A controlled increase in modulus or G' after the adhesive has been applied and cooled can be obtained. The increase in modulus is at least ten times the modulus (G') of the adhesive immediately after adhesive application and cooling. Further, we have found that novel adhesive compositions of this invention can be prepared from a tackifier-plasticizer composition, wherein the increase in modulus can be controlled by variation in the compatibility of plasticizer/tackifier combination and their amount, such that the modulus reaches steady state at a specific desired period after application. In other words, the maximum modulus can be attained within a few minutes after application, within about 60 minutes of application, or more than 4 hours of application, as desired. However, it is clear that the adhesives of this invention typically do not attain a final modulus until at least 5 to 10 minutes after adhesive application to the work piece and cooling. The adhesives of the invention can be applied without the constraints resulting from the nature of the conventional hot melts. The adhesives of the invention can be applied at an adhesive temperature below 250° F., preferably below 150° F., and, most preferably, below 125° F.

A hot melt adhesive with suitable "creep" or "cold flow" properties will have some tendency to flow in the temperature range of 25°–50° C., but this tendency should be controlled, as manifested by a controlled change in modulus (G') values.

The following are considered to be illustrative values of storage modulus (G') values. The values are to be measured and recorded just after application and cooling (application modulus), and after the modulus has increased to a final equilibrium value (high steady state modulus).

| Property | Values at 25–50° C. and 0.01–0.25 Hz |
|---|---|
| Application Modulus (G') | $4 \times 10^4$ to $50 \times 10^4$ dynes/cm$^2$ |
| High Steady State Modulus (G') | $40 \times 10^4$ to $35 \times 10^6$ dynes/cm$^2$ |

TEST METHOD FOR CONTROLLED INCREASING MODULUS SAMPLES SCOPE

This method has been developed to demonstrate and measure the phenomena of delayed and controlled modulus increase in samples of hot melt adhesive.

Materials and Equipment

1. Rheometric rheological dynamic spectrometer/model TC-2000
2. 1.25 cm radius disposable plates
3. Release paper or Teflon board The term storage modulus (G') and other related viscoelastic or rheological properties, such as loss tangent (tan delta), loss modulus (G"), and loss compliance (J'), are interrelated and are defined by established methods of dynamic mechanics. These rheological quantities are measured on samples approximately 2.5 mm in thickness placed between 25 cm parallel plate fixtures of a Rheometrics Rheological Spectrometer Model TC-2000.

Procedure for First Run of Samples

1. Melt sample in oven at 350° F. for 20–30 minutes.
2. Pour a puddle of adhesive onto release paper; try to avoid making bubbles.
3. Find a bubble-free portion of the sample and place it on the disposable plate of the RDS. Cut off the excess adhesive with either a razor blade or a scissors. Mark the plate with the sample ID and mark its bottom.
4. Place the sample in the bottom sample holder and tighten the set screw.
5. Place another disposable plate in the upper fixture and tighten the set screw.
6. Mark both plates to show where they were aligned in the fixture by marking a line on the plate directly under the slit on the RDS fixture.
7. Bring the armature down so that the upper plate just makes contact with the sample. Watch the normal force and make enough contact to just barely cause deflection on the needle.
8. Melt the sample by raising the temperature to 90°–100° C. This will vary depending on the softening point of the sample. Watch the sample and soften it as much as you dare so as not to cause it to drip out of the fixture.
9. Allow it to equilibrate for 10 minutes.
10. Start the time sweep by pressing the START button.
11. Immediately adjust the temperature setting to 25° C.
12. Watch the RDS to make sure that it gives readings for the time and temperature intervals. Also, be sure that the normal force scale remains between the green portion on the scale for optimal readings. Be sure that the normal force does not exceed 25%. Forces greater than this could damage the transducer.
13. When the run is complete, remove the sample by loosening the set screw for the upper fixture first. Be sure that the normal force is within 25% when lifting the fixture off of the sample plate. Again, forces greater than 25% may damage the transducer.
14. Mark the sample for the time of the run on the top plate.

| RDS Settings | Initial Settings (Day 1) |
|---|---|
| Purge | Air ↑ 40 psi (coil in ice bath) |
| Temperature | Equilibrate at 90–110° C. for 10 minutes depending on the sample. Then start the time sweep and immediately set the temperature to 25° C. |
| Rate | 1 rad/sec |
| Strain | 1% |
| Sweep Parameters | Total Time: 90 min. Time/Measurement: 60 min. |
| Test Geometry | Gap: 2–4 mm Radius: 1.25 cm |
| Print | G' G" Tandelta Temperature Torque Time |

Procedure for Subsequent Runs of Samples

1. Place the sample in the lower test fixture, making sure to line up the alignment mark on the plate with the lines in the fixture. Tighten the set screw.
2. Bring down the upper fixture and connect the sample in the holder. Make sure to watch so that the normal force does not exceed 25% so not to cause damage to the transducer. Tighten the set screw.
3. Set the gap width to the same setting use for measurement on DAY 1.
4. Make appropriate settings for a 30-minute time sweep at constant (25° C.) temperature.

| Settings for Day 1 | |
|---|---|
| Purge | Air ↑ 40 psi (coil in ice bath) |
| Temperature | 25° C. constant |
| Sweep Parameters | Total Time: 30 min. Time/Measurement: 3 min. |
| Test Geometry | Gap: Do NOT measure and reset the reading, use the reading found for the initial setting. Radius: 1.25 cm |

DETAILED DESCRIPTION OF THE INVENTION

The adhesive typically comprises a tackifying resin, which is typically aliphatic, aromatic, or aliphatic-aromatic in character, a solid plasticizer, and, optionally, an effective amount of thermoplastic polymer and an optional oil. The components are selected in proportions such that the adhesive exhibits varied properties as described above. The rate of property change can be controlled by selection of appropriate tackifying resin, or blend of resin, and plasticizer in proportions of tackifiers and plasticizer such that the desired modulus can reach its maximum value in a controlled period, i.e., from greater than about 10 minutes, 1 hour, 6 hours or more, after application.

We have found that these components cooperate to form an adhesive having improved properties. The adhesives can have low viscosity at application temperatures. The adhesive has extended open time, useful viscosity profile, and excellent wet and dry bond strength.

The typical compositions of these adhesives are set forth below in Tables I and II.

TABLE I

Low Polymer Resin Compositions

|  | Useful | Preferred | Most Preferred |
| --- | --- | --- | --- |
| Solid Plasticizer | 5–75 | 10–60 | 40–50 |
| Tackifier | 25–95 | 30–90 | 35–65 |
| Polymer | 0–15 | 0–12 | 0.1–10 |

TABLE II

Higher Polymer Resin Compositions

|  | Useful | Preferred | Most Preferred |
| --- | --- | --- | --- |
| Solid Plasticizer | 5–70 | 10–50 | 20–30 |
| Tackifier | 20–85 | 30–75 | 35–60 |
| Polymer | 10–55 | 12–35 | 15–30 |

Tackifying Resin

The adhesives of the invention contain a tackifying resin in combination with a thermoplastic polymer and the plasticizer. Tackifying resins useful in the adhesives of the invention comprise rosin derivatives including wood rosin, tall oil, tall oil derivatives, rosin ester resins, natural and synthetic terpenes and aromatic aliphatic or mixed aromatic-aliphatic tackifying resins. The tackifying resins are selected for a specific degree of compatibility with the plasticizer.

Aromatic monomers useful in forming the aromatic and aliphatic-aromatic adhesive compositions of the invention can be prepared from any monomer containing substantial aromatic qualities and a polymerizable unsaturated group. Typical examples of such aromatic monomers include the styrenic monomers styrene, alphamethylstyrene, vinyl toluene, methoxystyrene, t-butylstyrene, chlorostyrene, etc., indene monomers including indene, methyl indene, and others. Aliphatic monomers are typically natural and synthetic terpenes which contain $C_5$ and $C_6$ cyclohexyl or cyclopenyl saturated groups that can additionally contain a variety of substantially aliphatic ring substituents. Aliphatic tackifying resins can be made by polymerizing a feed stream containing sufficient aliphatic monomer such that the resulting resin exhibits aliphatic characteristics. Such feed streams can contain other aliphatic unsaturated monomers such as 1,3-butadiene, cis-1,3-pentadiene, trans-1,3-pentadiene, 2-methyl-1,3-butadiene, 2-methyl-2-butene, cyclopentadiene, dicyclopentadiene, terpene monomers, and others. Mixed aliphatic-aromatic resins contain sufficient aromatic monomers and sufficient aliphatic monomers and optionally other $C_3$–$C_8$ unsaturated monomers to produce a resin having both aliphatic and aromatic character.

The adhesive compositions of the invention can contain rosin and rosin derivatives as a tackifying agent. Rosin is a solid material that occurs naturally in the oleo resin of pine trees and typically is derived from the oleo resinous exudate of the living tree, from aged stumps and from tall oil produced as a by-product of kraft paper manufacture. After it is obtained, rosin can be treated by hydrogenation, dehydrogenation, polymerization, esterification, and others. Rosin is typically classed as a gum rosin, a wood rosin, and as a tall oil rosin. The materials can be used unmodified and additionally can be used in the form of esters of polyhydric alcohols and can be polymerized through the inherent unsaturation of the molecules. The materials are commercially available and can be blended into the adhesive compositions using standard blending techniques.

Representative examples of such rosin derivative tackifying resins include the pentaerythritol esters of tall oil, gum rosin, wood rosin or mixtures thereof.

Representative examples of such aliphatic resins include natural terpene resins, hydrogenated synthetic $C_9$ resins, hydrogenated synthetic $C_5$ resins, synthetic branched and unbranched $C_5$ resins, and mixtures thereof.

Representative examples of such aromatic-aliphatic tackifying resins include styrenated terpene resins, styrenated $C_5$ resins, or mixtures thereof.

The tendency of the adhesive to have rapidly changing properties or slowly changing properties relates to the compatibility of the tackifier/plasticizer combination. The variation in the compatibility of the components, primarily the tackifier (or tackifier blend) with the plasticizer, produces a variation in rate of change in properties to the equilibrium (ambient state) value. More compatible blends of tackifiers (or tackifier blends) and plasticizers tend to cause the properties to change (e.g., modulus increase) less rapidly. Less compatible blends result in more rapid change in properties. In other words, in a system containing largely aliphatic tackifying resins and aromatic tackifying resins with an aromatic plasticizer, increasing the proportion of aliphatic tackifying resin will lead to an increase in the rate of modulus development. Some guidance regarding compatibility can be obtained from solubility parameter data. Compositions with more similar solubility parameters will tend to be more compatible, while large differences will tend to indicate less compatibility Additionally, the chemical nature of the materials can aid in selecting components for desired compatibility. Increasing aromaticity in the tackifier will tend to increase compatibility, while an increasing aliphatic nature will tend to reduce compatibility with the aromatic plasticizers of the invention.

Plasticizer

A plasticizer is broadly defined as a typically organic composition that can be added to rubbers and other resins to improve extrudability, flexibility, workability, or stretchability. Typical plasticizers in adhesives are plasticizing oils that are liquid at typical ambient temperature. The plasticizer used in the adhesives of the invention is typically a solid composition at ambient temperature having a softening point of at least 45° C. Preferably, the plasticizer composition has a softening point of at least 60° C. Increased softening points (60°–130° C.) can aid in improving heat resistance or preventing bond failure at high temperatures.

One useful class of plasticizers used in the invention comprises a cyclo-aliphatic or aromatic ester of a benzene dicarboxylic acid. Such plasticizers are prepared by forming an ester from a cyclo-aliphatic or aromatic alcohol such as cyclohexanol, phenol, naphthol, or other monohydroxy alcohol compounds having from 5 to 12 carbon atoms. The ester compounds are formed from dicarboxylic acid compounds, typically phthalic acids. Phthalic acids that can be used in the plasticizers are 1,2-benzene dicarboxylic acid, 1,3-benzene dicarboxylic acid (isophthalic acid), or 1,4-benzene dicarboxylic acid (terephthalic acid). The preferred plasticizers of this class comprise dicyclohexyl phthalate or diphenyl phthalate. Most preferably, dicyctohexyl orthophthalate is used.

A second class of useful plasticizers comprise an aromatic carboxylic acid ester of a cycloaliphatic polyfunctional alcohol having 2 to 10 hydroxyl groups. Specific examples of preferred hydroxy compounds include glucose, fructose, sucrose, 1,4-cyclohexane dimethanol, and other useful cycloaliphatic polyfunctional hydroxyl compounds. Aromatic carboxylic acids that can be used with the cycloaliphatic polyfunctional alcohols to form this class of ester plasticizer compounds of the invention typically have at least one aromatic group and at least one carboxyl function. Representative acids include benzoic acid, naphthanoic acid, and 4-methyl benzoic acid.

The most preferred plasticizer is a solid with a softening point above 60° C. which belongs to the class of plasticizers including cyclohexane dimethanol dibenzoate compounds. A 1,4-cyclohexane dimethanol dibenzoate (containing cis- and trans- isomers) is exemplified and produces the maximum control over variation and change in adhesive physical properties.

The Thermoplastic Polymer Base

The thermoplastic polymer base that can be used in manufacturing the novel adhesives of this invention are thermoplastic polymers that have sufficient compatibility with the tackifier, plasticizer, and oil components to form a homogenous melt and solid. In the adhesive of high polymer content, thermoplastic material provides to the adhesive sufficient cohesive strength such that the adhesive, after application and attainment of maximum modulus, forms a cohesively competent adhesive bonding mass.

In the low polymer content materials, the polymer acts to control viscosity and to produce initial bond values. The plasticized low polymer system tends to reduce the initial $T_g$ resulting in a composition that machines well and has good initial tack. After reaching equilibrium, the $T_g$ is no longer suppressed and the adhesive can solidify into a somewhat competent mass.

Any of a variety of available thermoplastic materials can be used in the compositions of the invention. Examples of such thermoplastics are ethylene based polymers such as ethylene/vinyl acetate, ethylene acrylate, ethylene methacrylate, ethylene methyl acrylate, ethylene methyl methacrylate, copolymers of ethylene and 1-6 mono- or di-unsaturated monomers, polyamides, polybutadiene rubber, polyesters such as polyethylene terephthalate, polybutylene terephthalate, etc., thermoplastic polycarbonates, atactic poly-alpha-olefins, including atactic polyethylene, atactic polypropylene, and others; thermoplastic polyacrylamides, polyacrylonitrile, copolymers of acrylonitrile with other monomers such as butadiene, styrene, etc., polymethyl pentene, polyphenylene sulfide, aromatic polyurethanes; styrene-acrylonitrile, acrylonitrile-butadiene-styrene, styrene-butadiene rubbers, polyethylene terephthalate, acrylonitrile-butadiene-styrene elastomers, polyphenylene sulfide. Also, A—B, A—B—A, A—(B-A)$_n$—B, (A—B)$_n$—Y block copolymers wherein the A comprises a polyvinyl aromatic block, the B block comprises a rubbery midblock, and others can be used. The aromatic character of the polymers provide compatibility with the aromatic plasticizing agents discussed below and provide controlled compatibility with the tackifier or the tackifier blends used to control modulus in the adhesive compositions. The preferred polymers should have a molecular weight sufficient that, when used in an adhesive formulation, the adhesive can maintain a high cohesive strength.

Additionally, we have found that ethylene vinyl acetate thermoplastic polymers, preferably having about 5 to 50 wt % vinyl acetate and a melt index of at least 10, are also preferred for use in this invention. While the ethylene/vinyl acetate polymers have no aromatic character, they form compatible hot melt adhesives having controlled modulus physical property changes when applied in the end uses disclosed.

In the case of ethylene/vinyl acetate thermoplastic copolymers, the variation in properties obtained through the plasticizer tackifier combinations of the invention causes the ethylene/vinyl acetate based materials to be fluid initially because of a substantially reduced $T_g$ which slowly increases over time until the $T_g$ reaches a point wherein the material becomes no longer a fluid. In these systems, the peel strength of the adhesive can drop substantially over time. Generally, after 10 minutes, 3 hours, or 6 hours, depending on formulation, the peel strength drops to less than about one lb. per inch.

Other preferred polymers for use in the adhesives of this invention comprise linear A—B—A block, linear A—(B—A)$_n$—B multiblock copolymers, and radial or teleblock copolymers of the formula (A—B)$_n$—Y wherein A comprises a polystyrene block, B comprises a substantially rubbery polybutadiene or polyisoprene block, Y comprises a multivalent compound, and n is an integer of at least 3. The midblocks can be post-treated to improve their heat stability through hydrogenation or other post-treatment removing residual unsaturation. We believe that the size and the amount of the A or end blocks in the A—B—A block of copolymer structure should be as much as 15–51 wt % of the polymer.

While the total styrene content of the polymers can be as much as 51 wt % of the polymer, and since the polymers can have more than two A blocks for optional performance, the largest A block should be less than or equal to about 20 wt % of the polymer, and, most preferably, is less than or equal to 15 wt % of the polymer. In an S—B—S (styrene-butadienestyrene) copolymer, the preferred molecular weight is about 50,000 to 120,000, and the preferred styrene content is about 20 to 35 wt %. In an S—I—S (styrene-isoprene-styrene) copolymer, the preferred molecular weight is about 100,000 to 150,000 and the preferred styrene content is about 14–30 wt %. Hydrogenating the butadiene midblocks produces rubbery midblocks that are typically considered to be ethylenebutylene midblocks.

Such block copolymers are available from Shell Chemical Company, Enichem and Fina. Multiblock or tapered block copolymers (the A—(B—A)$_n$—B type) are available from Firestone under the STEREON 840A and 845 trademarks.

The adhesive compositions of the invention can contain other compatible polymers, fillers, pigments, dyes, oils, catalysts, inhibitors, antioxidants, UV absorbers, waxes, and other conventional additives.

In construction methods using the adhesives of the invention, the adhesives are typically applied from applicators such as spray heads, print wheels, or extruders that can deliver the adhesive at elevated temperatures (typically above about 250° F. and typically in the range of 275°–400° F.). Extruder applicators can apply a bead of adhesive in any arbitrary width. The width selected typically obtains a high quality bond with minimal adhesive application. Print wheels apply the adhesive in a pattern to a surface at sufficient add-on quantities to obtain high bond strength at minimal adhesive application. The spray heads have apertures that range from about 0.01 to about 0.04 inches. Under the operating conditions of typical adhesive spray machines, the diameter of the sprayed adhesive fiber can range from the size of the aperture to as little as about 0.001 inches depending on operating conditions.

Depending on the end use and final bond strength desired, the adhesive can be applied at amounts that range from 0.5 milligrams per square inch to as much as 10 milligrams per square inch. Extruded adhesive is applied at a rate of up to about 15 mg/linear inch or more. Preferably, because of the unique properties of the adhesives of this invention, the adhesives can be used at an application amount of from about 0.5 milligrams per square inch to 10 milligrams per square inch.

In the sealing of cigarette cartons, a low polymer adhesive composition of the invention is extruded in a bead or in discrete dots along a carton surface. The carton is closed by adhering a mating portion of the carton to the adhesive on the carton surface. Such low polymer adhesives maintain the integrity of the carton during manufacture but after storage, and attaining the equilibrium values of the adhesive composition, the carton is easily opened manually because the adhesive becomes brittle and the bond obtains a low peel strength with substantial sheer strength.

Similarly, in the use of a palletizing adhesive, small amounts of adhesive are applied to units placed in a palletized assembly. The small amounts of adhesive maintain the mechanical pallet integrity during the construction of the pallet and, after a time, the adhesive obtains its equilibrium value, causing the peel strength of the adhesive to reduce substantially, rendering the pallet easily disassembled at the use site.

Similarly, removable coupons can be applied to containers using the low polymer adhesives of the invention. Such coupons are attached to the containers with great integrity during bottling and labeling. Once distributed and purchased at a distribution site, the labels are easily removed because the adhesives reached low equilibrium peel value and are easily removed from the container without damage to the coupon.

The adhesive compositions of the invention, particularly the high polymer compositions, can be used in the manufacture of disposable articles. The high polymer content adhesives have the ability to penetrate the nonwoven of the disposable article because of their low modulus after cooling. The adhesive, before reaching a high equilibrium modulus, appears to be a soft liquid material. The low modulus of the high polymer adhesives causes the material to display excellent wetting properties resulting in high quality bonds with great integrity. The low initial modulus of the adhesive of the invention permits operators to spray the high polymer adhesives at relatively low temperatures because the materials retain significant fluidity before the materials reach the final equilibrium modulus. This is in sharp contrast to conventional hot melt sprays which are typically used at very high temperatures in order to maintain sufficient fluidity for penetration of porous substrates.

During the manufacture of disposable articles using the adhesives of the invention, two modes of application are preferred. One mode of operation involves spraying the adhesive upon a fabric, such as a tissue, a woven or nonwoven web, or other material having permeability to the adhesive. Such sprayed-on adhesive can penetrate the permeable tissue, nonwoven or woven fiber, to cause the sheet to be embedded in the adhesive and adhered to the substrate such as an absorbent layer, back layer, or film. Alternatively, the adhesives of the invention can be directly applied to back sheet or film and the tissue, woven or nonwoven fabric, or other material can be applied to the adhesive on the film. The adhesive retains sufficient liquidity that it can penetrate pores or apertures in the fabric to form a mechanical bond. In the manufacture of tissue fluff absorbent cores, the fluff is typically wrapped by tissue. The tissue layer can be wrapped around the fluff and can overlap. Adhesive can then be sprayed on the overlapping portion of tissue outerwrap, can penetrate the wrappings and adhere the tissue to the fluff ensuring that the fluff obtains dimensional stability from adherence to the outer wrap.

In somewhat greater detail, the sprayable, hot melt adhesive compositions of the invention typically comprise an effective amount of a tackifying agent and sufficient solid plasticizers of desired degree of compatibility and an effective amount of a thermoplastic polymer base to form an effective adhesive that has the unique property that, after spraying and cooling, can display a change in at least one physical property.

The hot melt adhesives of the invention are made in common hot melt manufacturing equipment. In the manufacture of the hot melt adhesives of the invention, the thermoplastic polymer is typically added to a melt comprising either the tackifier or the plasticizer material or mixtures thereof. Such additions facilitate the blending of the polymer into a smooth, uniform mixture. In such a manufacturing regimen, either the tackifier or the plasticizer or a portion thereof is added to the manufacturing equipment under inert atmosphere (with optional antioxidants) and is heated and agitated until melted. The thermoplastic polymer is then added to the melt at a rate such that the mixture forms a uniform smooth blend within a reasonable period. Antioxidant materials used in the manufacture of the adhesive can be added to the melt prior to, with, or after the addition of the polymer. Once a smooth blend of the polymer in conjunction with an adhesive component is formed, the balance of the components of the hot melt adhesives can be added at a convenient rate. Once the uniform blend of all the adhesive ingredients is formed, the adhesive can be drawn off and packaged in a convenient form including in drums, blocks, pillows, pellets, granules, etc. The following examples provide additional information with respect to the manufacture of the adhesives of the invention and include the best mode.

EXAMPLE I

Into a sigma blade mixer having a nitrogen atmosphere and heated to a temperature of 350° F. was added about 49.5 parts of styrenated terpene tackifying resin (ZONATAC 105) and 0.5 parts of an antioxidant (IRGANOX 1010). The mixer was operated until the antioxidant was fully blended with the molten tackifying resin. Into the tackifying resin was added 25 parts of a styrene-butadiene-styrene block copolymer having 37 wt % styrene (KRATON D-1122, Shell Chemical Co.). After the copolymer had been fully added to the resin and a uniform melt resulted, 25 parts of a 1,4-dicyclohexane dimethanol dibenzoate (Benzoflex 352) were added. The sigma blade mixer was operated until the contents were a smooth melt blend and the material was withdrawn and packaged.

EXAMPLE II

Following the procedure of Example I, the following compositions were blended into a hot melt adhesive:

| Ingredient | Trade Name | Parts |
|---|---|---|
| S-B-S | KRATON 1122 | 25 |
| Antioxidant | IRGANOX 1330 | 0.5 |
| Tackifying agent | PERMALYN 603 | 49.5 |
| 1,4-Dicyclohexane-dimethanoldibenzoate | BENZOFLEX 352 | 25 |

EXAMPLE III

Following the procedure of Example I, the following compositions were blended into a hot melt adhesive:

| Ingredient | Trade Name | Parts |
|---|---|---|
| S-B-S | KRATON 1122 | 25 |
| Antioxidant | IRGANOX 1010 | 0.5 |
| Tackifying agent | PERMALYN 603/ ZONATAC 501 Blend | 24.75/ 24.75 |
| 1,4-Dicyclohexane-dimethanoldibenzoate | BENZOFLEX 352 | 25 |

EXAMPLE IV

Following the procedure of Example I, the following compositions were blended into a hot melt adhesive:

| Ingredient | Trade Name | Parts |
|---|---|---|
| S-I-S | SOL T-193B | 30 |
| Antioxidant | IRGANOX 1010 | 0.5 |
| Tackifying agent | REGALREZ 1094 | 49.5 |
| 1,4-Dicyclohexane-dimethanoldibenzoate | BENZOFLEX 352 | 20 |

EXAMPLE V

Example IV was repeated except that PERMALYN 603 was substituted for REGALREZ 1094.

EXAMPLE VI

Following the procedure of Example II, the following compositions were blended into a hot melt adhesive:

| Ingredient | Trade Name | Parts |
|---|---|---|
| S-E-B-S | KRATON G 1652 | 25 |
| Antioxidant | IRGANOX 1010 | 0.5 |
| Tackifying agent | REGALREZ 1094 | 49.5 |
| 1,4-Cyclohexane-dimethanoldibenzoate | BENZOFLEX 352 | 25 |

EXAMPLE VII

Example VI was repeated except that PERMALYN 603 was substituted for REGALREZ 1094.

EXAMPLE VIII

Following the procedure of Example II, the following compositions were blended into a hot melt adhesive:

| Ingredient | Trade Name | Parts |
|---|---|---|
| E/VA (28% VA; MI = 20) | ELVAX 250 | 30 |
| Antioxidant | IRGANOX 1010 | 0.5 |
| Tackifying agent | PERMALYN 603 | 49.5 |
| 1,4-Cyclohexane-dimethanoldibenzoate | BENZOFLEX 352 | 20 |

EXAMPLE IX

Example VIII was repeated except that PERMALYN 603 was substituted for ZONATAC 501.

Example X

Following the procedure of Example XIII, the following compositions were blended into a hot melt adhesive:

| Ingredient | Trade Name | Parts |
|---|---|---|
| E/VA (28% VA; MI equals 20) | ELVAX 250 | 30 |
| Antioxidant | IRGANOX 1010 | 0.5 |
| Tackifying agent | PERMALYN 603/ ZONATAC 501 Light Blend | 49.5 |
| 1,4-Cyclohexane-dimethanoldibenzoate | BENZOFLEX 352 | 20 |

EXAMPLE XI

Following the procedure of Example I, the following compositions were blended into a hot melt adhesive:

| Ingredient | Trade Name | Grams |
|---|---|---|
| S-B-S/S-I-S Blend | KRATON 1102 & KRATON 1117 | 5/14 |
| Antioxidant | ETHANOX 330 | 1.0 |
| Tackifying agent | ZONATAC 501 | 59 |
| 1,4-Dicyclohexane-dimethanoldibenzoate | BENZOFLEX 352 | 21 |

EXAMPLE XII

Fugitive Palletizing Hot Melt Adhesive Generally Following the Procedure of Example I The following compositions were blended into a hot melt adhesive:

| Ingredient | Trade Name | Parts |
|---|---|---|
| Coumarin-Indene Tackifying Resin | NEVEX 110 | 40.9 |
| Black Colorant | VINSOL Resin | 2.0 |
| Antioxidant | IRGANOX 1076 | 1.0 |
| Ethylene Vinyl Acetate Resin | ELVAX 150 | 10.0 |
| Plasticizing Agent | BENZOFLEX 352 | 45.0 |

* ELVAX 150, 33 wt-% vinyl acetate and 40 melt index

EXAMPLE XIII

Fugitive Palletizing Hot Melt Adhesive Generally Following the Procedure of Example I The following compositions were blended into a hot melt adhesive:

| Ingredient | Trade Name | Parts |
| --- | --- | --- |
| Tackifying Resin | ESCOREZ 7312 | 48.0 |
| Antioxidant | IRGANOX 1076 | 1.0 |
| Ethylene Vinyl Acetate Resin | ELVAX 150 | 10.0 |
| Plasticizing Agent | BENZOFLEX 352 | 39.9 |

The product of Example XIII was prepared and extruded onto a corrugated paperboard substrate in a uniform line of about 3/16" diameter. Additional pieces of the corrugated paperboard substrate were then placed over the glue line after an open time of 5 minutes. The additional substrate layers were compressed with a roller. The pieces were then peeled from the adhesive line at time intervals of 1 hour. Upon the application of substantial peel force, the substrates were removed only with substantial force and straining of the adhesive. After 4 hours, the substrate was removed with little peel force with no fiber tearing or straining of the adhesive.

A second set of experiments were done with the adhesive of Example XIII. A 3/16" diameter bead was applied to a corrugated substrate. A second corrugated sheet was contacted with the bead. The corrugated sheet was scored with a blade, creating a 90 degree flap of board. The assembled board substrates were inserted with a peel tester and pulled apart at 300 ft/min. A duplicate set of assembled substrates were made. The first set were tested within 1 hour of preparation and showed strong fiber treating bonds of about 6 to 10 lb/inch. The second set were pulled at 15 hours after preparation and failed adhesively at about 1 to 1.5 lb/inch.

The modulus of the comparative Example A shown in the bottom of Table I is at its maximum value at the earliest time wherein the modulus can be measured after the adhesive is tested. In sharp comparison to the modulus of comparative Example A, the modulus of Examples 1–10 shows more or less rapid increase in modulus over the testing period. It should be noted that the format of the data, for example, 2.4 E + 0.8 is representative of number $2.4 \times 10^8$.

These data clearly indicate that the selection of thermoplastic block copolymer, tackifier, or tackifier blend, and plasticizer can exert significant and important control over a storage modulus of the adhesive.

TABLE III

| DSC EXAMPLES (wt-%) | | | |
| --- | --- | --- | --- |
| PERMALYN 603 | WT 95 | BENZOFLEX 352 | OIL |
| DSC 1 | 57 | 0 | 29 | 14 |
| DSC 2 | 43 | 14 | 29 | 14 |
| DSC 3 | 28.5 | 28.5 | 29 | 14 |
| DSC 4 | 14 | 43 | 29 | 14 |
| DSC 5 | 0 | 57 | 29 | 14 |
| DSC 6 | 0 | 0 | 100 | 0 |

The above tackifier/plasticizer oil combinations were prepared to determine the effect of the compatibility of the materials on change in modulus after cooling. These examples and the change in their properties in a heating or cooling cycle were investigated with differential scan calorimetry. DSC is a technique that follows the thermal changes associated with thermal transitions, such as curing, melting, crystallization, etc. Initially, four scans were made on each sample. The first was a dynamic heating scan at 10° per minute over the temperature range, −42°+150° C. The second run was a programmed cooling scan made at 5° per minute from 150° to −40° C. The third run was a reheating scan of the material in the second run made again at 10° per minute over the range −40° to 150° C. The sample was then rapidly cooled from 150° C. at 200° per minute, and a fourth heating run of the quenched, cooled sample was made at 10° per minute over the range of −40° to 150° C.

The first run is a melt profile of the sample which reflects the change in modulus caused by crystal growth associated with the previous cooling history. The second run is an attempt to follow the crystallization of the sample as it is slowly cooled. The third run was made to determine the effect the slow cooling had on the sample properties. The fourth run was made after the sample was quickly cooled to the amorphous state in order to limit crystallization. FIGS. 1 through 4 are the four runs discussed above for DSC 6 100% Benzoflex 352. These scans indicate that Benzoflex 352 readily crystallizes under normal conditions. The remaining figures are scans of blended materials showing the effect of the presence of the tackifier and oil in the compositions on crystal formation.

FIGS. 5 through 9 are the first run profiles for DSC 1 through 5. Each scan exhibits two glass transitions ($T_g$'s) and a single melt endotherm. These curves for the formulated materials are distinguished from the Benzoflex curve by the presence of two glass transition temperatures, the total amount of heat fusion required for the melt, and the temperature of the peaks on the scan. Clearly, when heated in a dynamic mode, the material melts in a substantially different mode from the pure plasticizer material.

The second DSC runs, for which there are no figures showing the scans of a programmed cooling run, notes no crystallization of any hot melt samples. This is in sharp contrast with the crystallization noted in FIG. 2 of Benzoflex 352.

Figure 15:
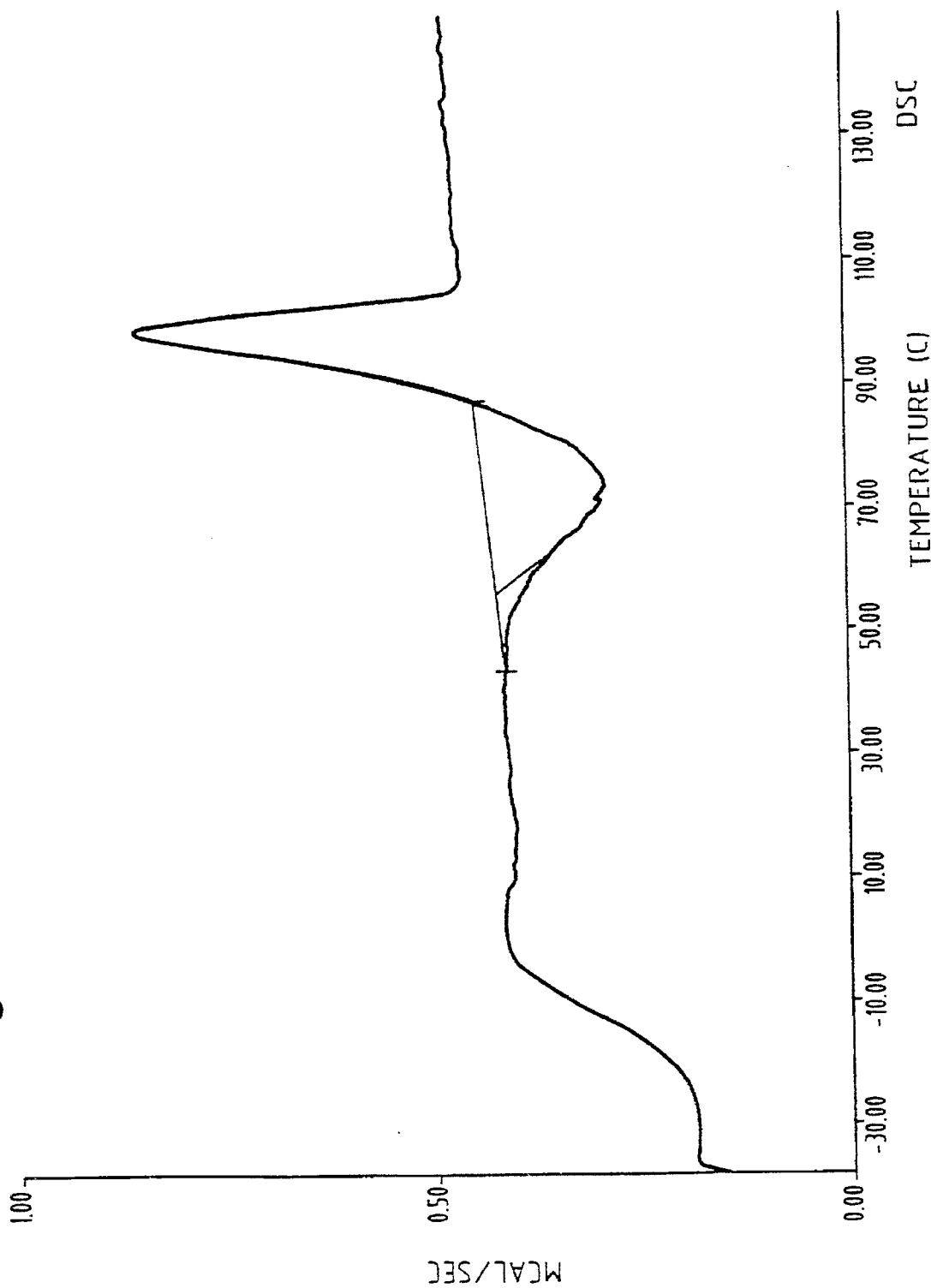
Figure 16:
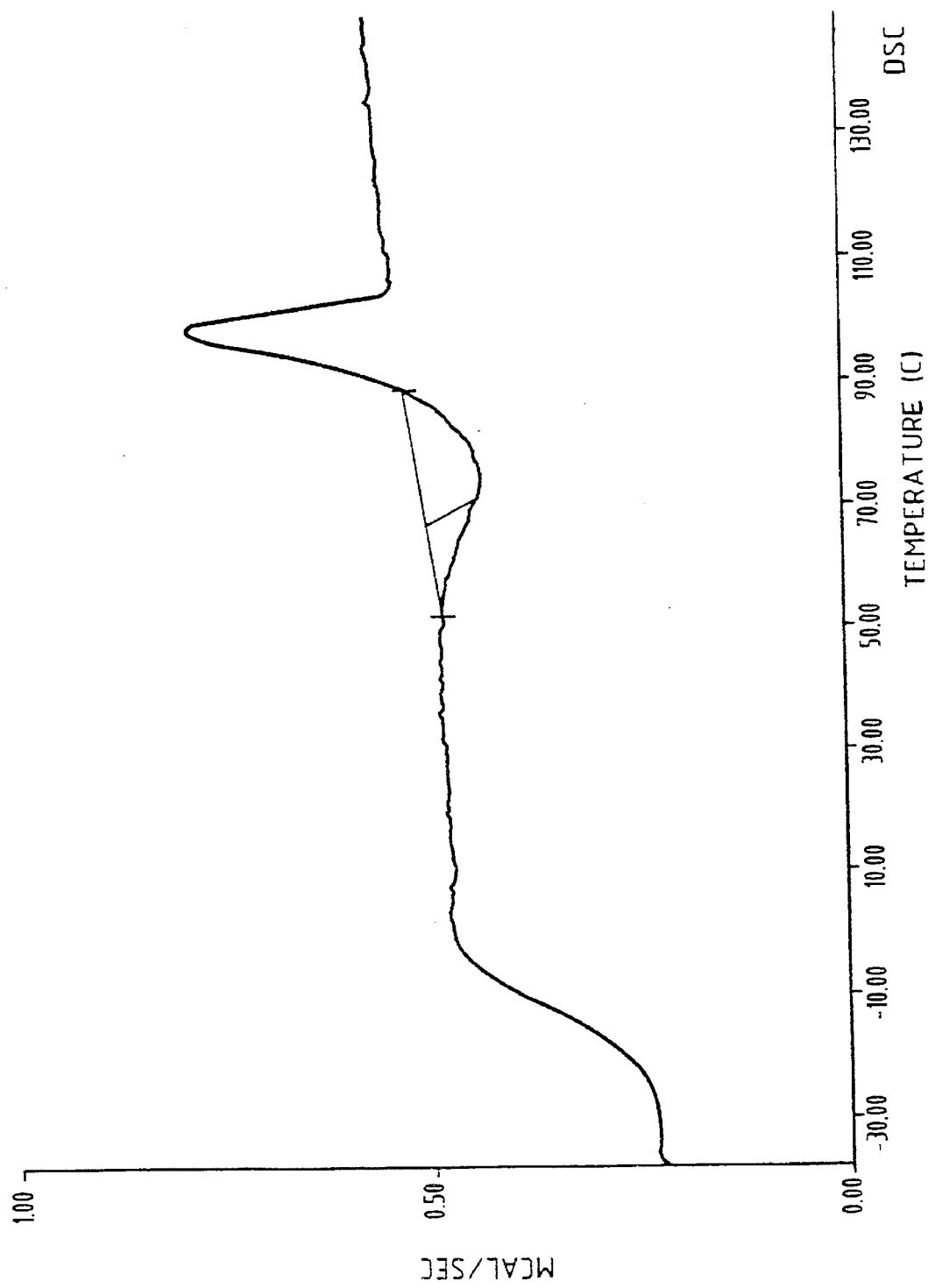
Figure 17:
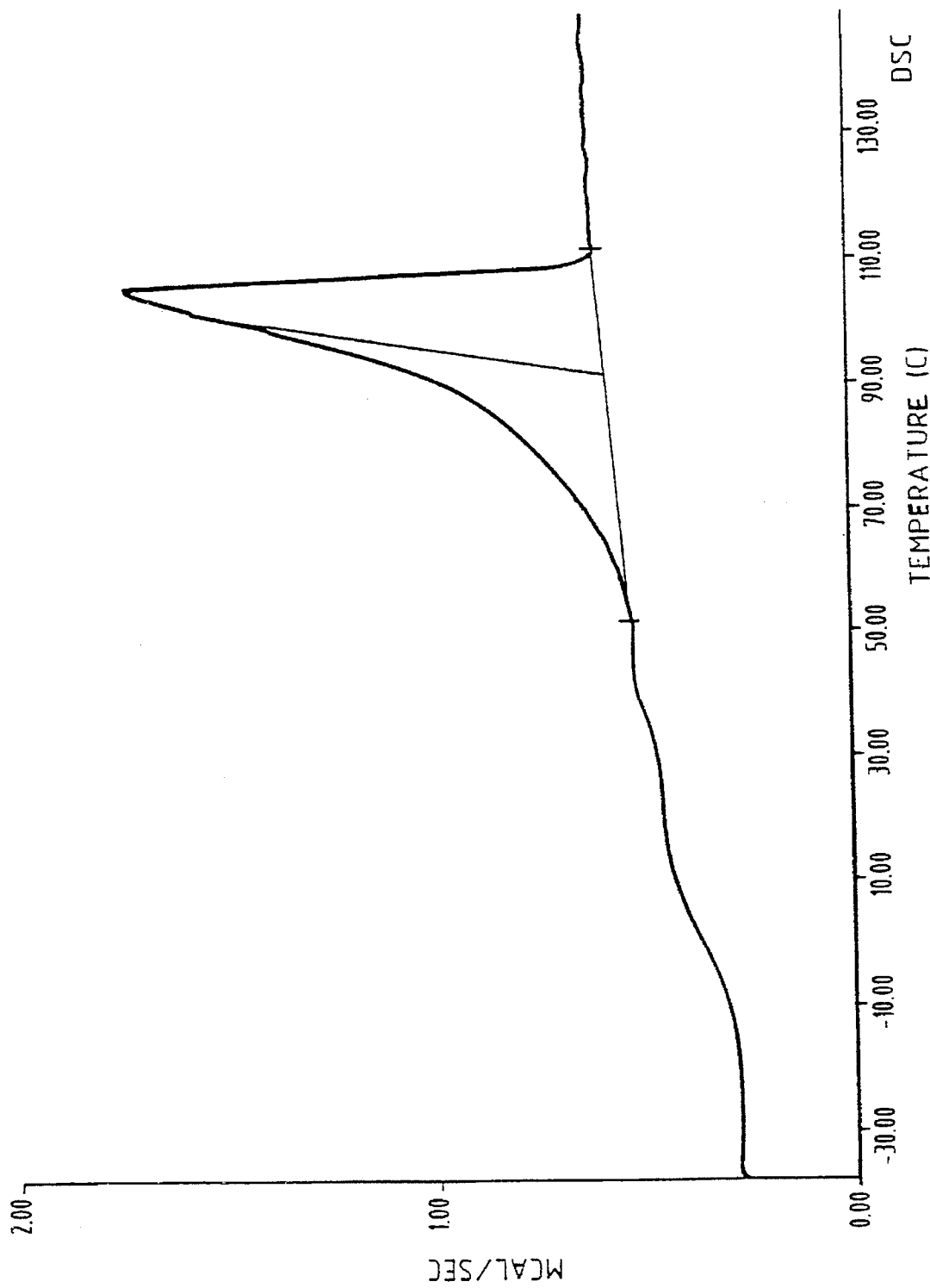
Figure 18:
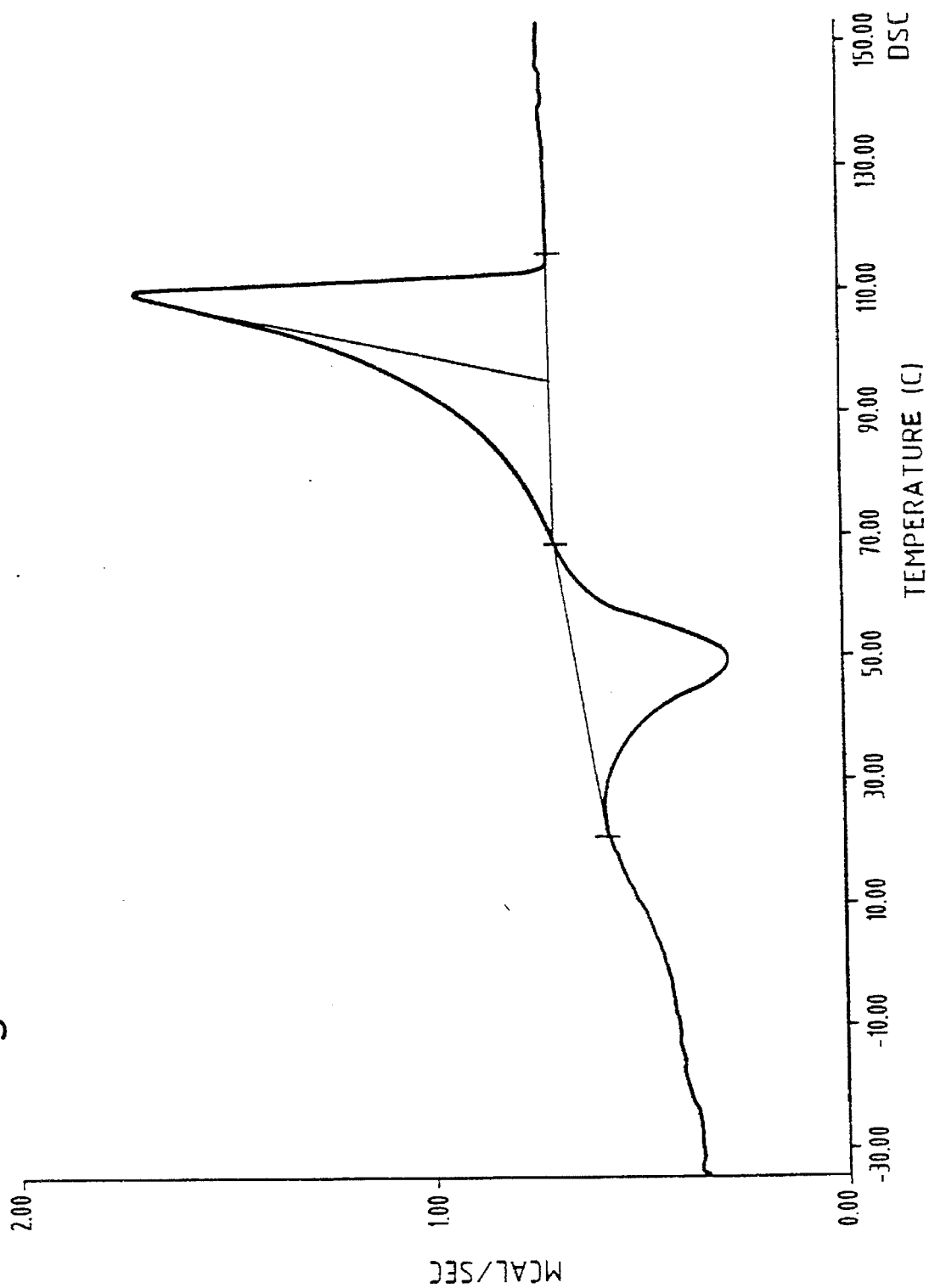
Figure 19:
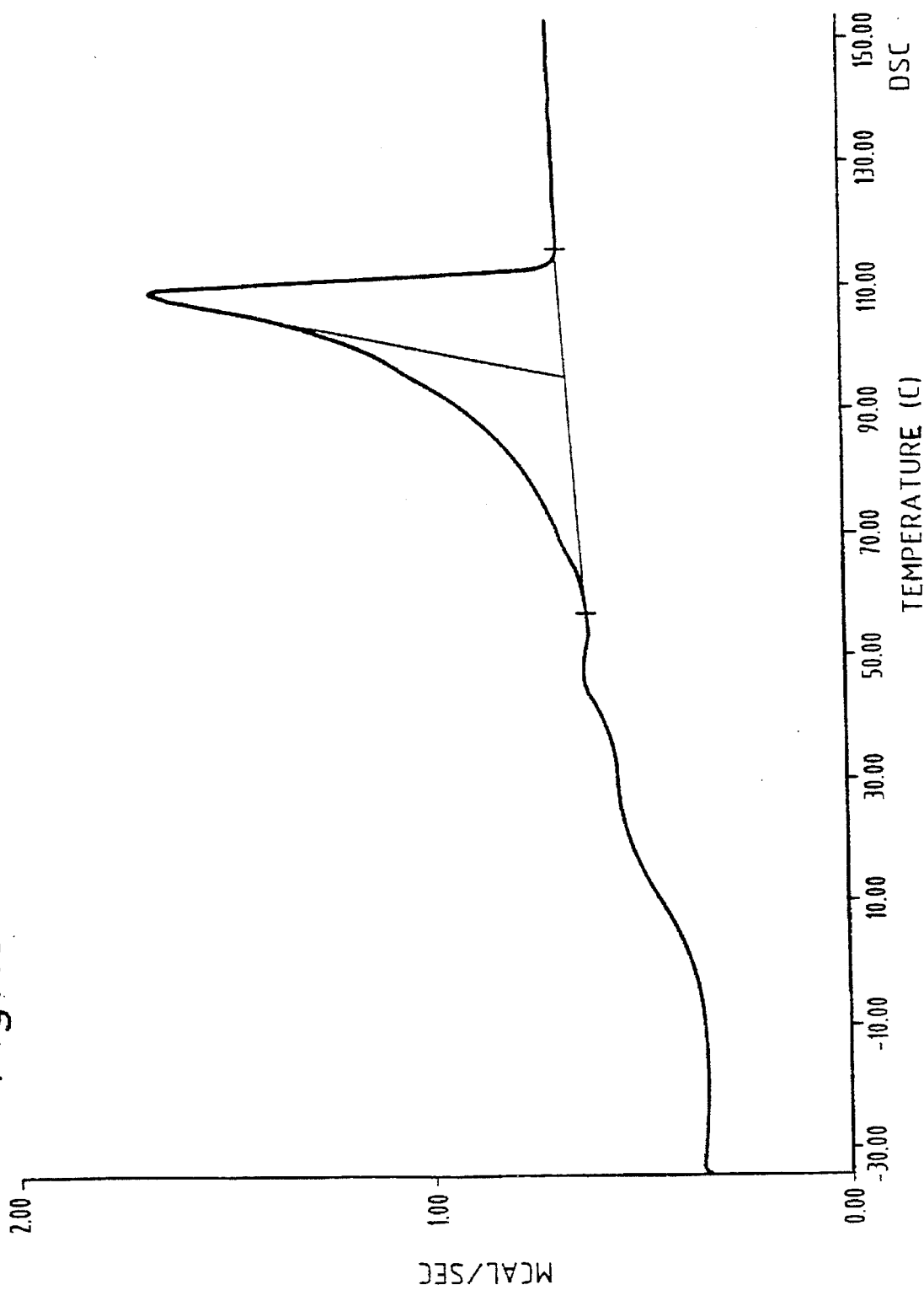

FIGS. 10 through 14 show an exothermic crystallization peak that immediately precedes an endothermic melting peak in the DSC run as discussed above. These scans show a cold crystallization phenomenon. Cold crystallization is the phenomenon observed when a molecule, generally polymeric molecule, is cooled quickly enough past its crystallization temperature and is frozen or super cooled in an amorphous state. Thermodynamically, these systems prefer particular order and, upon heating, reach a temperature where there is sufficient energy and mobility to rearrange into a crystal structure. The exotherms show such a cold crystallization. This cold crystallization shows that the resin oil combinations hinder crystallization considerably and effects a change in modulus for a period of time after the sample reaches ambient temperature. In order to determine the time period required for the hot melt samples to reach full modulus with full crystallization at 25° C., the samples were quenched cooled from 150° to 25° C. at 200° per minute and allowed to crystallize at 25° C. for various times, namely, 1 hour, 1.5 hours, 2 hours, and 5 hours. A melt profile was then run for each sample, after its respective times, and the resulting curves were evaluated. FIGS. 15 and 16 show that the samples DSC 1 and DSC 2 did not fully crystallize after even 5 hours as evidenced by the cold crystallization exotherms in the scan. Sample DSC 3 showed complete crystallization after 1 hour. FIG. 17 displays no cold crystallization exotherm before the endotherm peak. FIGS. 18 and 19 show that sample DSC 4 crystallizes between 1 hour and 1.5 hours. The 1 hour curve on FIG. 18 has an exotherm showing that the sample is not fully crystallized, while FIG. 19 shows full crystallization.

Figure 20:
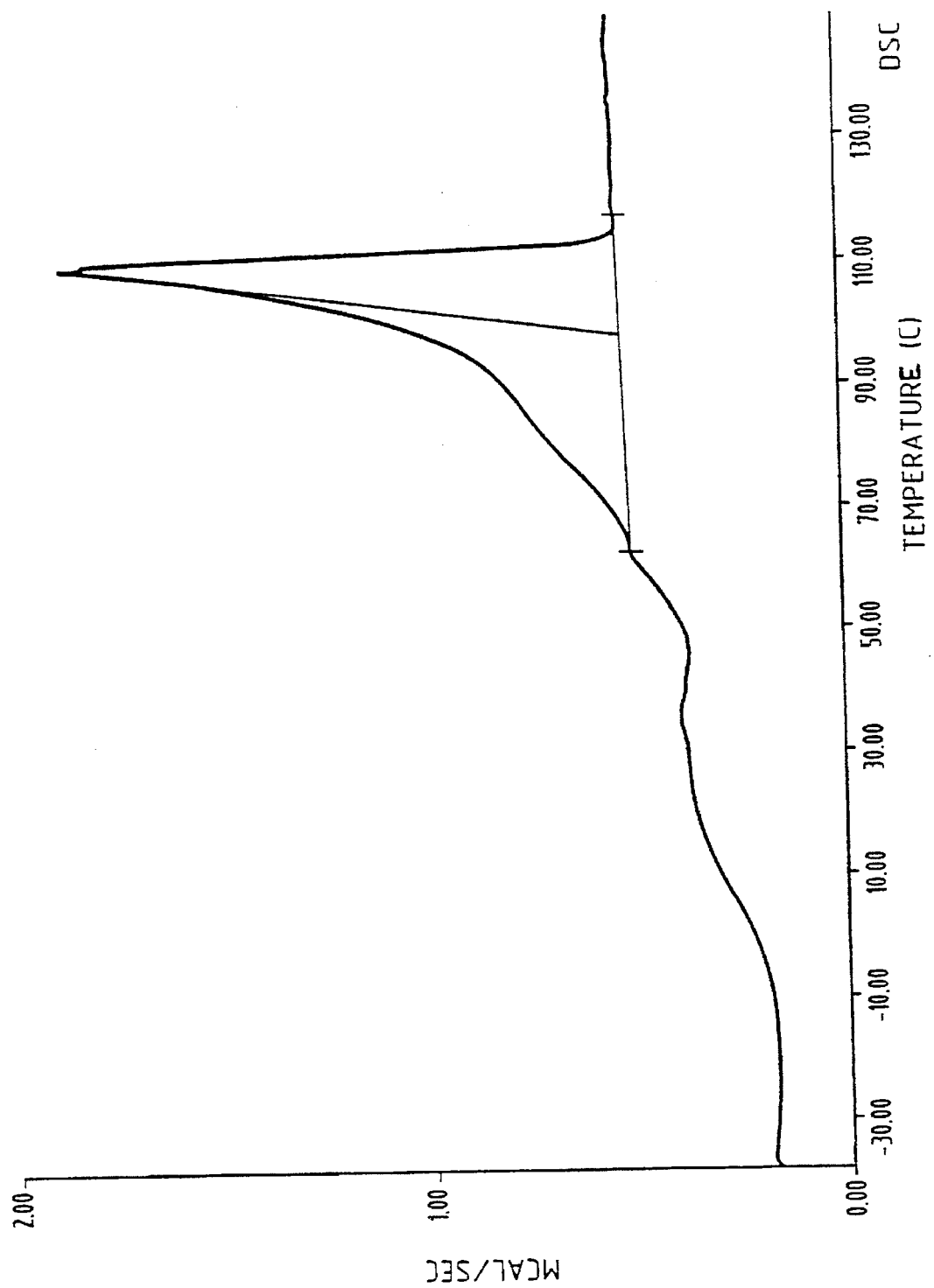

FIG. 20 shows that sample DSC 5 is fully crystallized after 1 hour. From these curves, it is clear that the time for crystallization and the associated increase in modulus can be controlled through careful blending of components and control over ingredient proportions.

While the above specification, examples, and data provide a basis for understanding specific examples and preferred embodiments of the invention, a variety of embodiments of the invention can be made without departing from the spirit and scope of the invention. Accordingly, the invention resides in the claims hereinafter appended.

We claim:

1. A cigarette carton secured by an effective amount of a hot melt adhesive composition comprising:
   (a) about 5 to 40 wt % of a cyclohexane dimethanol dibenzoate plasticizer;
   (b) about 20 to 80 wt % of a tackifier selected from the group consisting of an aromatic tackifying resin, aromatic-aliphatic tackifying resin, aliphatic tackifying resin, rosin derived tackifying resin, and mixtures thereof;
   (c) about 5 to 35 wt % of a thermoplastic polymer; wherein the composition, after application, cold flows for a controllable period of time at ambient temperature prior to subsequently increasing in modulus (G').

2. A pallet comprising an assembly of cartons secured by an effective amount of a hot melt adhesive composition comprising:
   (a) about 5 to 40 wt % of a cyclohexane dimethanol dibenzoate plasticizer;
   (b) about 20 to 80 wt % of a tackifier selected from the group consisting of an aromatic tackifying resin, aromatic-aliphatic tackifying resin, aliphatic tackifying resin, rosin derived tackifying resin, and mixtures thereof;
   (c) about 5 to 35 wt % of a thermoplastic polymer; wherein the composition, after application, cold flows for a controllable period of time at ambient temperature prior to subsequently increasing in modulus (G').

3. A disposable article having an absorbent layer covered by an outer wrap secured by an effective amount of a hot melt adhesive composition comprising:
   (a) about 5 to 40 wt % of a cyclohexane dimethanol dibenzoate plasticizer;
   (b) about 20 to 80 wt % of a tackifier selected from the group consisting of an aromatic tackifying resin, aromatic-aliphatic tackifying resin, aliphatic tackifying resin, rosin derived tackifying resin, and mixtures thereof;
   (c) about 5 to 35 wt % of a thermoplastic polymer; wherein the composition, after application, cold flows for a controllable period of time at ambient temperature prior to subsequently increasing in modulus (G').

4. The article of claim 3 wherein the article is a feminine pad.

5. The article of claim 3 wherein the article is a disposable diaper.

* * * * *